United States Patent
Heim-Riether et al.

(10) Patent No.: US 9,139,567 B2
(45) Date of Patent: Sep. 22, 2015

(54) ARYLPYRAZOLE ETHERS AS INHIBITORS OF LEUKOTRIENE A4 HYDROLASE

(75) Inventors: Alexander Heim-Riether, Biberach an der Riss (DE); Anil Kumar Padyana, Oxford, CT (US); Shuang Liang, Danbury, CT (US); Steven John Taylor, Southbury, CT (US); Qiang Zhang, Woodbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/233,520

(22) PCT Filed: Jul. 17, 2012

(86) PCT No.: PCT/US2012/047024
§ 371 (c)(1),
(2), (4) Date: Mar. 20, 2014

(87) PCT Pub. No.: WO2013/012844
PCT Pub. Date: Jan. 24, 2013

(65) Prior Publication Data
US 2014/0221373 A1    Aug. 7, 2014

Related U.S. Application Data

(60) Provisional application No. 61/509,155, filed on Jul. 19, 2011.

(51) Int. Cl.
C07D 403/12  (2006.01)
C07D 401/14  (2006.01)
C07D 405/14  (2006.01)
C07D 413/14  (2006.01)
C07D 231/12  (2006.01)
C07D 401/12  (2006.01)
C07D 405/12  (2006.01)
C07D 409/12  (2006.01)
C07D 413/12  (2006.01)
C07D 417/12  (2006.01)
C07D 471/04  (2006.01)
C07D 513/04  (2006.01)

(52) U.S. Cl.
CPC ............ C07D 403/12 (2013.01); C07D 231/12 (2013.01); C07D 401/12 (2013.01); C07D 401/14 (2013.01); C07D 405/12 (2013.01); C07D 405/14 (2013.01); C07D 409/12 (2013.01); C07D 413/12 (2013.01); C07D 413/14 (2013.01); C07D 417/12 (2013.01); C07D 471/04 (2013.01); C07D 513/04 (2013.01)

(58) Field of Classification Search
None
See application file for complete search history.

(56) References Cited

U.S. PATENT DOCUMENTS

| 4,918,092 | A | 4/1990 | Frenette et al. |
| 5,120,758 | A | 6/1992 | Satoh |
| 6,180,637 | B1 | 1/2001 | Schindler et al. |
| 7,098,222 | B2 | 8/2006 | Altenbach et al. |
| 7,429,665 | B2 | 9/2008 | Verhoest et al. |
| 7,674,802 | B2 | 3/2010 | Sandanayaka et al. |
| 8,551,982 | B2 | 10/2013 | Abeywardane et al. |
| 2002/0132822 | A1 | 9/2002 | Noe et al. |
| 2006/0019269 | A1 | 1/2006 | Helgadottir et al. |
| 2006/0223792 | A1 | 10/2006 | Butler et al. |
| 2007/0066820 | A1 | 3/2007 | Sandanayaka et al. |
| 2007/0149544 | A1 | 6/2007 | Sandanayaka et al. |
| 2013/0196973 | A1 | 8/2013 | Abeywardane et al. |
| 2013/0236468 | A1 | 9/2013 | Bylock |

(Continued)

FOREIGN PATENT DOCUMENTS

| WO | 9610999 A2 | 4/1996 |
| WO | 9611192 A1 | 4/1996 |
| WO | 2004056369 A1 | 7/2004 |

(Continued)

OTHER PUBLICATIONS

Davies, D. R. et al., "Discovery of Leukotriene A4 Hydrolase Inhibitors Using Metabolomics Biased Fragment Crystallography +", Journal of Medicanal Chemistry, vol. 52, No. 15, Aug. 13, 2009, pp. 4694-4715.

(Continued)

*Primary Examiner* — Timothy R Rozof
(74) *Attorney, Agent, or Firm* — Michael P. Morris; David L. Kershner; Usha R. Patel

(57) ABSTRACT

The present invention relates to compounds of formula I or a pharmaceutically acceptable salt thereof, wherein $A^1, A^2, A^3, L^1, L^2$ and D are as defined herein. The compounds of formula (I) are useful as inhibitors of leukotriene $A_4$ hydrolase (LTA4H) and treating LTA4H related disorder. The present invention also relates to pharmaceutical compositions comprising the Compounds of formula (I), methods of using these compounds in the treatment of various diseases and disorders, and processes for preparing these compounds.

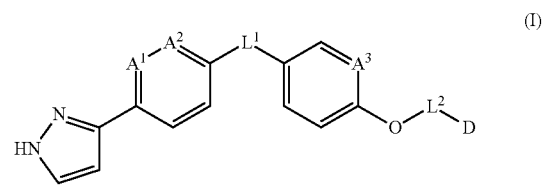

(I)

19 Claims, No Drawings

(56) References Cited

U.S. PATENT DOCUMENTS

| | | |
|---|---|---|
| 2013/0244996 A1 | 9/2013 | Abeywardane et al. |
| 2014/0031339 A1 | 1/2014 | Abeywardane et al. |

FOREIGN PATENT DOCUMENTS

| | | |
|---|---|---|
| WO | 2007040682 A1 | 4/2007 |
| WO | 2011114220 A1 | 9/2011 |
| WO | 2012125598 A1 | 9/2012 |
| WO | 2013012844 A1 | 1/2013 |
| WO | 2014014874 A1 | 1/2014 |

OTHER PUBLICATIONS

Grice, C.A. et al., "Current Status of Leukotriene A4 Hydrolase Inhibitors". Expert Opinion on Therapeutic Patents, vol. 18, No. 12, Dec. 1, 2008, p. 1333-1350.

International Search Report for PCT/US2012/047024 mailed Sep. 20, 2012.

Minami, M. et al., "Molecular Cloning of a cDNA Coding for Human Leukotriene A4 Hydrolase". The Journal of Biological Chemistry, vol. 262, No. 29, 1987, p. 13873-13876.

Sandanayaka, V. et al., "Discovery of 4-[(2 S)-2-{[4-(4-Chlorophenoxy)phenoxy]methyl}-1-pyrrolidinyl]butanoic Acid (DG-051) as a Novel Leukotriene B4 Biosynthesis". Journal of Medicinal Chemistry, vol. 53, No. 2, Jan. 28, 2010, p. 573-585.

Sandanayaka, V. et al., "Discovery of novel leukotriene A4 hydrolase inhibitors based on piperdine and piperazine scaffolds". Bioorganice and Medicinal Chemistry Letters, Pergamon, Elsevier Science, GB, vol. 20, n0 9, May 1, 2010, pp. 2851-2854.

Thangapandian, Sundarapandian et al., "Molecular Docking and Pharacophore Filtering in the Discovery of Dual-Inhibitors for Human Leukotreine A4 Hydrolase and Leukotriene C4 Synthase", Journal of Chemical Information and Modeling, vol. 51, No. 1, Jan. 24, 2011, pp. 33-44.

U.S. Appl. No. 14/330,297, filed Jul. 14, 2014—Inhibitors of Leukotriene Production. Inventor: Asitha Abeywardane et al.

U.S. Appl. No. 14/330,307, filed Jul. 14, 2014—Inhibitors of Leukotriene Production. Inventor: Asitha Abeywardane et al.

ARYLPYRAZOLE ETHERS AS INHIBITORS OF LEUKOTRIENE A4 HYDROLASE

FIELD OF THE INVENTION

This invention relates to arylpyrazole ethers that are useful as inhibitors of leukotriene $A_4$ hydrolase ($LTA_4H$) and are thus useful for treating a variety of diseases and disorders that are mediated or sustained through the activity of leukotrienes including asthma, allergy and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LT) are oxidized lipids that are produced by several cell types including neutrophils, mast cells, eosinophils, basophils, monocytes and macrophages. The first committed step in the intracellular synthesis of LTs involves oxidation of arachidonic acid by 5-lipoxygenase (5-LO) to leukotriene $A_4$ ($LTA_4$), a process requiring the 5-lipoxygenase-activating protein (FLAP). Leukotriene $A_4$ hydrolase ($LTA_4H$) catalyzes the hydrolysis of $LTA_4$ to produce leukotriene $B_4$ ($LTB_4$). Through the engagement of the $LTB_4$ receptors (BLT1, BLT2), $LTB_4$ stimulates an array of pro-inflammatory responses (leukocyte chemotaxis, cytokine release, etc.). The leukotriene pathway has been implicated in diseases in which inflammation is a critical component of the pathology; these include cancer, asthma, atherosclerosis, colitis, glomerularnephritis, and pain (for a review, see M. Peters-Golden and W. R. Henderson, Jr., M.D., N. Engl. J. Med., 2007, 357, 1841-1854).

BRIEF SUMMARY OF THE INVENTION

The present invention provides novel compounds which inhibit leukotriene $A_4$ hydrolase ($LTA_4H$) and are thus useful for treating a variety of diseases and disorders that are mediated or sustained through the activity of leukotrienes, including allergic, pulmonary, fibrotic, inflammatory and cardiovascular diseases and cancer.

In one embodiment, the invention relates to a compound of formula (I):

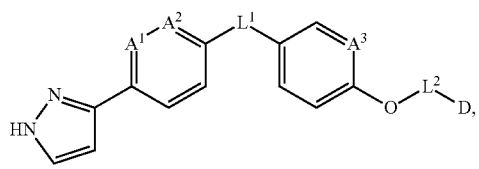

I or a pharmaceutically acceptable salt thereof, wherein:
$A^1$, $A^2$ and $A^3$ are each independently CH or N;
$L^1$ is a linker selected from —O— and —$CH_2$—;
$L^2$ is absent or a —($C_1$-$C_6$)alkylene-linker; wherein said —($C_1$-$C_6$)alkylene-linker is optionally substituted with one to three groups selected from —OH, halo, —($C_1$-$C_6$)alkyl;
D is a ring selected from
(a) —($C_3$-$C_7$)cycloalkyl, ($C_6$-$C_{10}$)aryl, and -(5- to 11-membered)heteroaryl;

(b) -(4- to 11-membered)heterocycloalkyl, comprising an O or S ring atom and optionally 1 to 3 additional ring heteroatoms selected from N, O, and S;

(c) 4-8 member monocyclic heterocyclic comprising a N ring atom and 1 to 3 additional ring heteroatoms selected from N, O, and S;

(d) a 6 to 11-membered fused bicyclic, bridged bicyclic or spirocyclic heterocyclic radical comprising a N ring atom and optionally 1 to 3 additional ring heteroatoms selected from N, O, and S; and (e) a group selected from 2-oxo-pyrrolidin-1-yl, 2-oxo-pyrrolidin-3-yl, 2-oxo-pyrrolidin-5-yl, 1-methyl-2-oxo-pyrrolidin-4-yl, and 2-oxo-piperidin-5-yl wherein each of said D rings is optionally substituted with one to three $R^1$ groups; and wherein each of said D rings is further optionally substituted, where possible, by one or two groups independently selected from (=O) and (=S);

each $R^1$ is independently selected from halo, —OH, —$CF_3$, —CN, —($C_1$-$C_6$)alkyl, —O($C_1$-$C_6$)alkyl, —C(O)$R^2$, —C(O)O$R^2$, —C(O)N($R^2$)$_2$, —N($R^2$)$_2$, —N($R^2$)C(O)$R^2$, —S(O)$_2$$R^2$, —N($R^2$)—S(O)$_2$—$R^2$, —($C_3$-$C_6$)cycloalkyl, -(5- to 11-membered)heterocycloalkyl, —($C_6$-$C_{10}$)aryl, and -(5- to 11-membered)heteroaryl; wherein each of said, —($C_1$-$C_6$)alkyl, —O($C_1$-$C_6$)alkyl, —($C_3$-$C_6$)cycloalkyl, -(5- to 11-membered)heterocycloalkyl, —($C_6$-$C_{10}$)aryl, and -(5- to 11-membered)heteroaryl of said $R^1$ group is optionally substituted with one to three groups selected from halo, —OH, —$CF_3$, —($C_1$-$C_6$)alkyl, —C(O)OH, —C(O)O$C_1$-$C_6$)alkyl, —C(O)($C_1$-$C_6$)alkyl), —$NH_2$, —NH($C_1$-$C_6$)alkyl, N(($C_1$-$C_6$)alkyl)$_2$ and —CN;

each $R^2$ is independently selected from the group consisting of —H, —($C_1$-$C_6$)alkyl, —($C_3$-$C_6$)cycloalkyl, -(5- to 11-membered)heterocycloalkyl, —($C_6$-$C_{10}$)aryl, and -(5- to 11-membered)heteroaryl; wherein each of said, —($C_1$-$C_6$)alkyl, —O($C_1$-$C_6$)alkyl, —($C_3$-$C_6$)cycloalkyl, -(5- to 11-membered)heterocycloalkyl, —($C_6$-$C_{10}$)aryl, and -(5- to 11-membered)heteroaryl of said $R^2$ group is optionally independently substituted by one to three groups selected from halo, —OH, —$CF_3$, —($C_1$-$C_6$)alkyl, —$NH_2$, —NH($C_1$-$C_6$)alkyl, —N(($C_1$-$C_6$)alkyl)$_2$ and —CN.

This invention also relates to pharmaceutical compositions comprising the compounds of formula (I), methods of using these compounds in the treatment of various diseases and disorders, processes for preparing these compounds, and intermediates useful in these preparative processes.

DETAILED DESCRIPTION OF THE INVENTION

It will be understood that the terms "compounds of formula (I)" and "compounds of the invention" have the same meaning unless indicated otherwise.

In its broadest embodiment (Embodiment 1), the invention relates to compounds of formula (I), and pharmaceutically acceptable salts thereof, as described above in the summary of the invention.

Embodiment 2

In another embodiment, the invention relates to a compound of formula (I) as described in Embodiment 1, or a pharmaceutically acceptable salt thereof, wherein $A^1$, $A^2$ and $A^3$ are each CH.

Embodiment 3

In another embodiment, the invention relates to a compound of formula (I) as described in Embodiment 1, or a pharmaceutically acceptable salt thereof, wherein $A^1$ and $A^3$ are each CH, and $A^2$ is N.

Embodiment 4

In another embodiment, the invention relates to a compound of formula (I) as described in Embodiment 1, or a pharmaceutically acceptable salt thereof, wherein $A^1$ and $A^2$ are each CH, and $A^3$ is N.

Embodiment 5

In another embodiment, the invention relates to a compound of formula (I) as described in Embodiment 1, or a pharmaceutically acceptable salt thereof, wherein $A^2$ and $A^3$ are each CH, and $A^1$ is N.

Embodiment 6

In another embodiment, the invention relates to a compound of formula (I) as described in any of the Embodiments 1-5, or a pharmaceutically acceptable salt thereof, wherein $L^1$ is —O—.

Embodiment 7

In another embodiment, the invention relates to a compound of formula (I) as described in any of the Embodiments 1-5, or a pharmaceutically acceptable salt thereof, wherein $L^1$ is —CH$_2$—.

Embodiment 8

In another embodiment, the invention relates to a compound of formula (I) as described in any of the Embodiments 1-7, or a pharmaceutically acceptable salt thereof, wherein $L^2$ is absent.

Embodiment 9

In another embodiment, the invention relates to a compound of formula (I) as described in any of the Embodiments 1-7, or a pharmaceutically acceptable salt thereof, wherein $L^2$ is a —(C$_1$-C$_6$)alkylene-linker; and wherein said —(C$_1$-C$_6$) alkylene-linker is optionally substituted with one to three groups selected from —OH, halo, —(C$_1$-C$_6$)alkyl.

Embodiment 10

In another embodiment, the invention relates to a compound of formula (I) as described in any of the Embodiments 1-8, or a pharmaceutically acceptable salt thereof, wherein $L^2$ is methylene, ethylene, or propylene; and wherein each of said methylene, ethylene and propylene is optionally substituted with methyl.

Embodiment 11

In another embodiment, the invention relates to a compound of formula (I) as described in any of the Embodiments 1-10, or a pharmaceutically acceptable salt thereof, wherein said D is a ring selected from —(C$_3$-C$_7$)cycloalkyl, (C$_6$-C$_{10}$) aryl, and -(5- to 11-membered)heteroaryl; wherein each of said —(C$_3$-C$_7$)cycloalkyl, (C$_6$-C$_{10}$)aryl, and -(5- to 11-membered)heteroaryl is optionally substituted with one to three $R^1$ groups; and wherein each of said —(C$_3$-C$_7$)cycloalkyl, (C$_6$-C$_{10}$)aryl, and -(5- to 11-membered)heteroaryl is further optionally substituted, where possible, by one or two groups independently selected from (=O) and (=S).

Embodiment 12

In another embodiment, the invention relates to a compound of formula (I) as described in any of the Embodiments 1-10, or a pharmaceutically acceptable salt thereof, wherein said ring D is a -(4- to 11-membered)heterocycloalkyl comprising an O or S ring atom and optionally 1 to 3 additional ring heteroatoms selected from N, O, and S; wherein said -(4- to 11-membered)heterocycloalkyl is optionally substituted with one to three $R^1$ groups; and wherein said -(4- to 11-membered)heterocycloalkyl is further optionally substituted, where possible, by one or two groups independently selected from (=O) and (=S).

Embodiment 13

In another embodiment, the invention relates to a compound of formula (I) as described in any of the Embodiments 1-10, or a pharmaceutically acceptable salt thereof, wherein said ring D is a 4-8 member monocyclic heterocyclic comprising a N ring atom and 1 to 3 additional ring heteroatoms selected from N, O, and S; wherein said 4-8 member monocyclic heterocyclic is optionally substituted with one to three $R^1$ groups; and wherein said 4-8 member monocyclic heterocyclic is further optionally substituted, where possible, by one or two groups independently selected from (=O) and (=S).

Embodiment 14

In another embodiment, the invention relates to a compound of formula (I) as described in any of the Embodiments 1-10, or a pharmaceutically acceptable salt thereof, wherein said ring D is a 6 to 11-membered fused bicyclic, bridged bicyclic or spirocyclic heterocyclic radical comprising a N ring atom and optionally 1 to 3 additional ring heteroatoms selected from N, O, and S; wherein said 6 to 11-membered fused bicyclic, bridged bicyclic or spirocyclic heterocyclic radical is optionally substituted with one to three $R^1$ groups; and wherein said 6 to 11-membered fused bicyclic, bridged bicyclic or spirocyclic heterocyclic radical is further optionally substituted, where possible, by one or two groups independently selected from (=O) and (=S).

Embodiment 15

In another embodiment, the invention relates to a compound of formula (I) as described in any of the Embodiments 1-10, wherein said ring D is selected from 2-oxo-pyrrolidin-1-yl, 2-oxo-pyrrolidin-3-yl, 2-oxo-pyrrolidin-5-yl, 1-methyl-2-oxo-pyrrolidin-4-yl, and 2-oxo-piperidin-5-yl; wherein each of said 2-oxo-pyrrolidin-1-yl, 2-oxo-pyrrolidin-3-yl, 2-oxo-pyrrolidin-5-yl, 1-methyl-2-oxo-pyrrolidin-4-yl, and 2-oxo-piperidin-5-yl is optionally substituted with one to three $R^1$ groups; and wherein each of said selected from 2-oxo-pyrrolidin-1-yl, 2-oxo-pyrrolidin-3-yl, 2-oxo-pyrrolidin-5-yl, 1-methyl-2-oxo-pyrrolidin-4-yl, and 2-oxo-piperidin-5-yl is further optionally substituted, where possible, by one or two groups independently selected from (=O) and (=S).

Embodiment 16

In another embodiment, the invention relates to a compound of formula (I) as described in any of the Embodiments 1-10, or a pharmaceutically acceptable salt thereof, wherein said ring D is selected from:

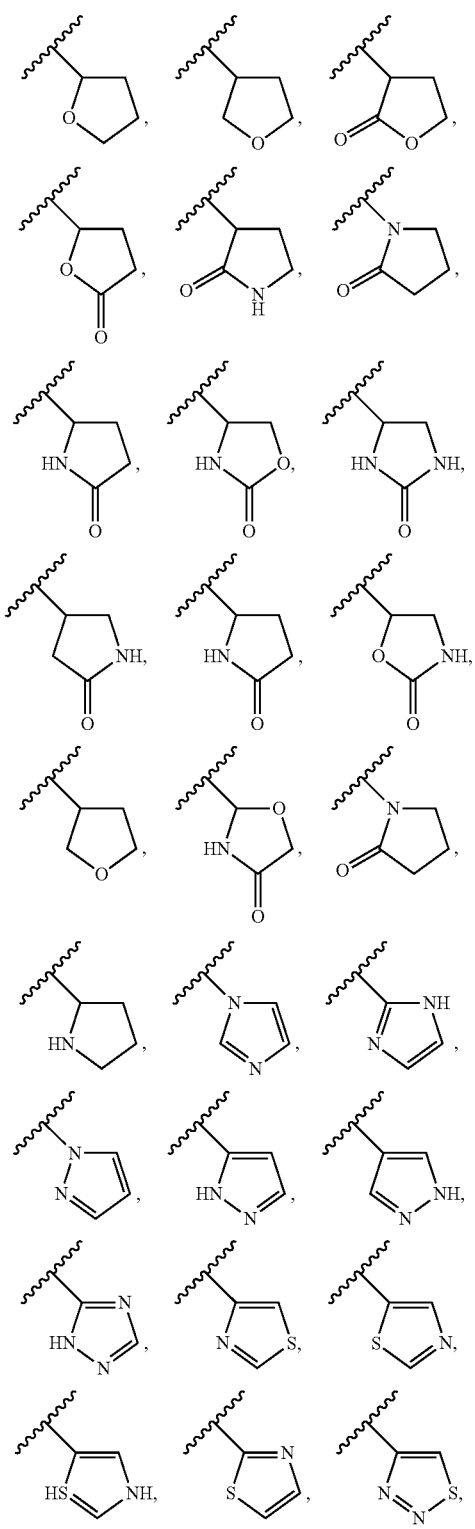

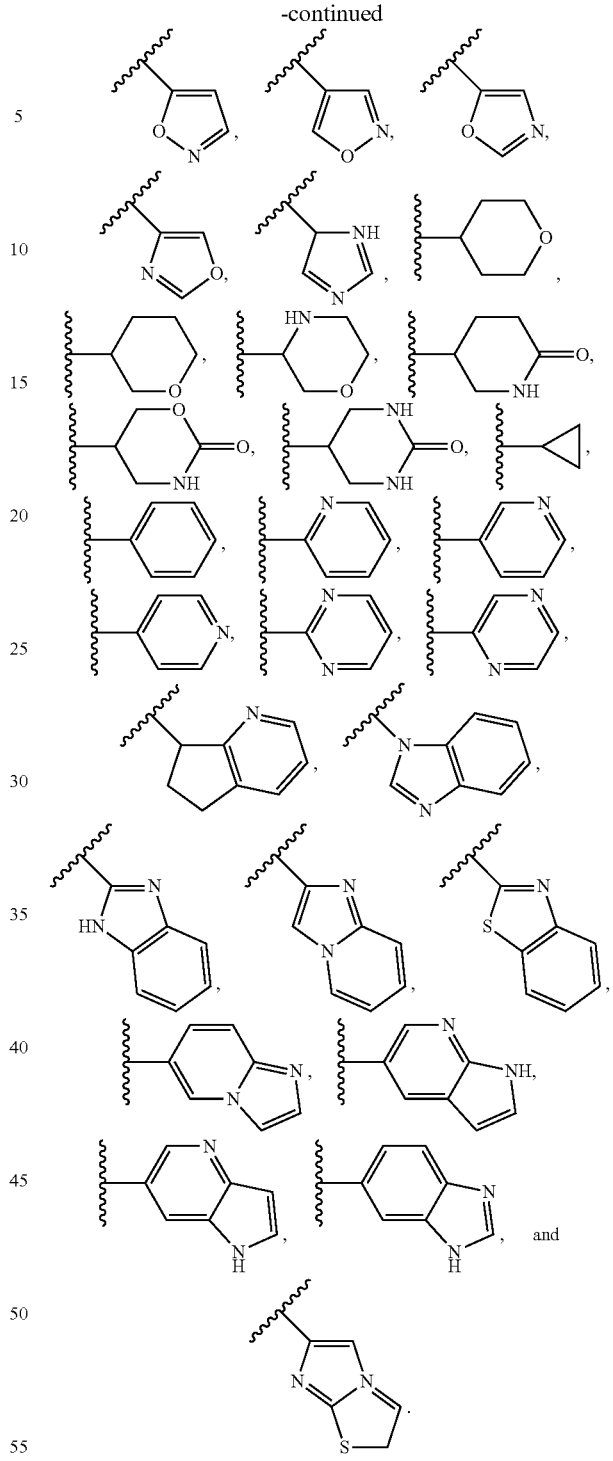

wherein each of the aforementioned D rings is optionally substituted by one to three $R^1$ groups.

Embodiment 17

In another embodiment, the invention relates to a compound of formula (I) as described in any of the Embodiments 1-4, or a pharmaceutically acceptable salt thereof, wherein $L^2$ and D taken together represent a group selected from:

(1-methyl-pyrrolidin-2-on-4-yl)methyl;
(pyrrolidin-2-on-3yl)oxy;
(pyrrolidin-2-on-5-yl)methyloxy;
2-(pyrrolidin-2-on-1-yl)ethyloxy;
3-(pyrrolidin-2-on-1-yl)propyloxy;
(tetrahydrofuran-3-yl)oxy;
(tetrahydrofuran-2-yl)methyloxy;
(tetrahydrofuran-3-yl)methyloxy; (piperidin-2-on-5-yl)oxy;
(1,3-oxazolidin-2-on-4-yl)methyloxy;
(1,3-oxazolidin-2-on-5-yl)methyloxy;
(morpholin-3-yl)methyloxy;
(morpholin-4-yl)ethyloxy;
1H-pyrazol-5-yl;
(1H-pyrazol-5-yl)methyloxy;
(1H-pyrazol-3-yl)methyloxy;
(1-methyl-1H-pyrazol-3-yl)methyloxy;
(1-methyl-1H-pyrazol-5-yl)methyloxy;
(1-methyl-2-(2-furyl)-pyrazol-5-yl)methyloxy;
3-(1H-pyrazol-1-yl)-ethyloxy;
2-(1H-pyrazol-4-yl)-ethyloxy;
3-(1H-pyrazol-1-yl)-3-methylpropyloxy;
(furan-2-yl)methyloxy;
(furan-3-yl)methyloxy;
(dihydrofuran-2(3H)-on-3-yl)oxy;
(dihydrofuran-2(3H)-on-5-yl)methyloxy;
(pyridin-3-yl)methyloxy;
(pyridin-4-yl)methyloxy;
(2-(1H-pyrazol-1-yl)-pyridin-5-yl)methyloxy;
1-(pyridin2-yl)-ethyloxy;
2-(pyridin-2-yl)ethyloxy;
2-(pyridin-3-yl)ethyloxy;
2-(pyridin-4-yl)-ethyloxy;
(pyrimidin-2-yl)methyloxy;
(thien-3-yl)methyloxy;
2-(thien-2-yl)ethyloxy;
(tetrahydro-2H-pyran-3-yl)oxy;
(tetrahydro-2H-pyran-4-yl)oxy);
(tetrahydro-2H-pyran-2-yl)methyloxy;
(tetrahydro-2H-pyran-3-yl)methyloxy;
(tetrahydro-2H-pyran-4-yl)methyloxy;
2-(tetrahydro-2H-pyran-2-yl)ethyloxy;
2-(tetrahydro-2H-pyran-4-yl)ethyloxy;
(2-methyl-1H-imidazol-1-yl)ethyloxy;
(pyrazin-2-yl)methyloxy;
benzyloxy;
(4-(methylsulfonyl)benzyl)oxy;
(1,3-thiazol-2-yl)methyloxy;
(1,3-thiazol-5-yl)methyloxy;
2-(1,3-thiazol-5-yl)ethyloxy;
(4-methyl-1,2,3-thiadiazol-5-yl)methyloxy;
(isoxazol-5-yl)methyloxy;
2-(isoxazol-4-yl)ethyloxy;
(1-methyl-1,2,4-triazol-5-yl)methyloxy;
(1,3-oxazol-4-yl)methyloxy;
(1,3-oxazol-5-yl)methyloxy;
(2-methyl-1,3-oxazol-4-yl)methyloxy;
(4-methyl-1,3-oxazol-5-yl)methyloxy;
(1H-benzimidazol-2-yl)methyloxy;
(1H-benzimidazol-5-yl)methyloxy;
(1H-benzimidazol-1-yl)ethyloxy;
(1H-benzimidazol-2-yl)ethyloxy;
2-((1H-benzimidazol-2-yl)-amino)ethyloxy;
(imidazo[2,1-b][1,3]thiazol-2-yl)methyloxy;
(1H-pyrrolo[2,3-b]pyridin-5-yl)methyloxy;
(6,7-dihydro-5H-cyclopenta[b]pyridin-7-yl)oxy;
2-(1H-pyrrolo[3,2-b]pyridin-6-yl)-ethyloxy;
(imidazo[1,2-a]pyridin-2-yl)methyloxy;
(1,3-benzothiazol-2-yl)methyloxy; and
(imidazo[1,2-a]pyridin-6-yl)methyloxy.

The following are exemplary compounds of the invention which can be made by the general synthetic schemes and examples described below, and methods known in the art.

TABLE 1

Exemplary compounds of the invention.

| Ex. No. | Structure | Name |
|---|---|---|
| 1 | 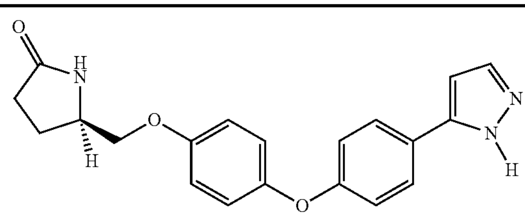 | (5R)-5-({4-[4-(1H-pyrazol-5-yl)phenoxy]phenoxy}methyl)pyrrolidin-2-one |
| 2 | 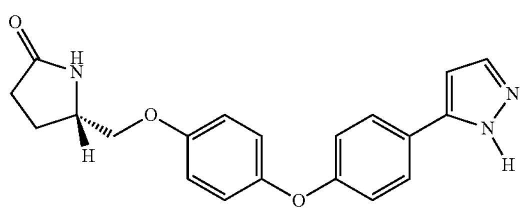 [SMILES: O=C1CC[C@@H](COc2ccc(Oc3ccc(-c4ccn[nH]4)cc3)cc2)N1] | (5S)-5-({4-[4-(1H-pyrazol-5-yl)phenoxy]phenoxy}methyl)pyrrolidin-2-one |
| 3 | 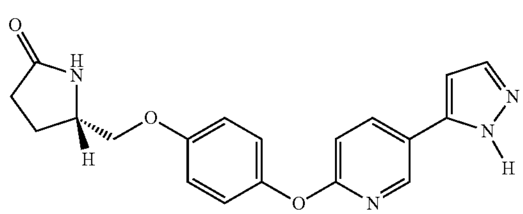 [SMILES: O=C1CC[C@@H](COc2ccc(Oc3ccc(-c4ccn[nH]4)cn3)cc2)N1] | (5S)-5-[(4-{[5-(1H-pyrazol-5-yl)pyridin-2-yl]oxy}phenoxy)methyl]pyrrolidin-2-one |

TABLE 1-continued

Exemplary compounds of the invention.

| Ex. No. | Structure | Name |
|---|---|---|
| 4 | 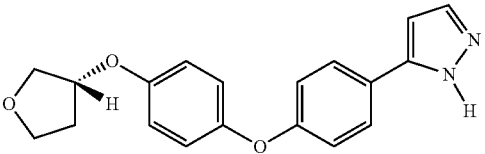 [SMILES: c1cc(-c2ccc(Oc3ccc(O[C@@H]4CCOC4)cc3)cc2)[nH]n1] | 5-(4-{4-[(3R)-tetrahydrofuran-3-yloxy]phenoxy}phenyl)-1H-pyrazole |
| 5 | 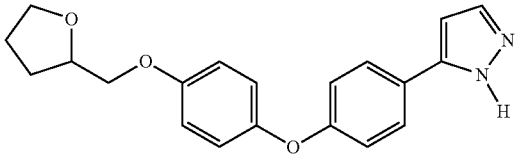 [SMILES: c1cc(-c2ccc(Oc3ccc(OCC4CCCO4)cc3)cc2)[nH]n1] | 5-{4-[4-(tetrahydrofuran-2-ylmethoxy)phenoxy]phenyl}-1H-pyrazole |
| 6 | 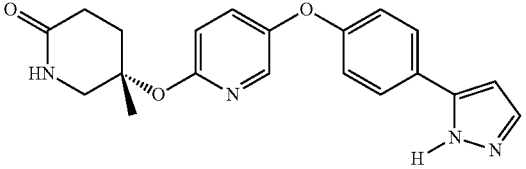 [SMILES: C[C@]1(Oc2ccc(Oc3ccc(-c4ccn[nH]4)cc3)cn2)CCC(=O)NC1] | (5S)-5-({5-[4-(1H-pyrazol-5-yl)phenoxy]pyridin-2-yl}oxy)piperidin-2-one |
| 7 | 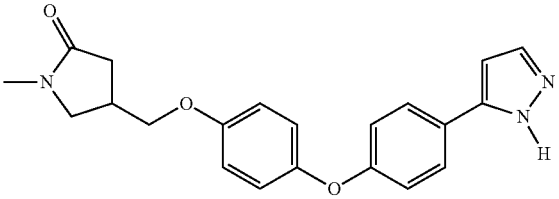 [SMILES: CN1CC(COc2ccc(Oc3ccc(-c4ccn[nH]4)cc3)cc2)CC1=O] | 1-methyl-4-({4-[4-(1H-pyrazol-5-yl)phenoxy]phenoxy}methyl)pyrrolidin-2-one |
| 8 | 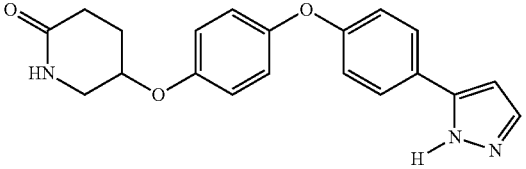 [SMILES: O=C1CCC(Oc2ccc(Oc3ccc(-c4ccn[nH]4)cc3)cc2)CN1] | 5-{4-[4-(1H-pyrazol-5-yl)phenoxy]phenoxy}piperidin-2-one |
| 9 | 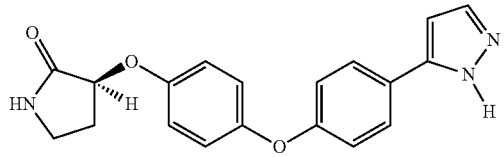 [SMILES: O=C1NCC[C@@H]1Oc1ccc(Oc2ccc(-c3ccn[nH]3)cc2)cc1] | (3S)-3-{4-[4-(1H-pyrazol-5-yl)phenoxy]phenoxy}pyrrolidin-2-one |
| 10 | 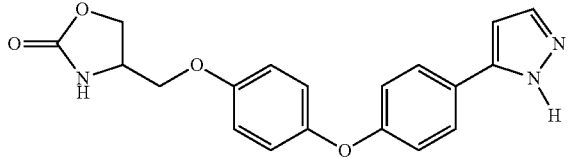 [SMILES: O=C1NC(COc2ccc(Oc3ccc(-c4ccn[nH]4)cc3)cc2)CO1] | 4-({4-[4-(1H-pyrazol-5-yl)phenoxy]phenoxy}methyl)-1,3-oxazolidin-2-one |
| 11 | 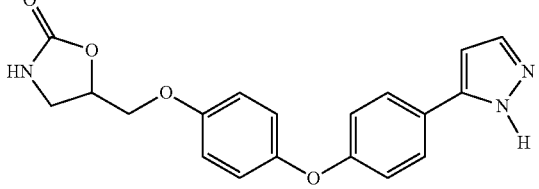 | 5-({4-[4-(1H-pyrazol-5-yl)phenoxy]phenoxy}methyl)-1,3-oxazolidin-2-one |

TABLE 1-continued

Exemplary compounds of the invention.

| Ex. No. | Structure | Name |
|---|---|---|
| 12 | 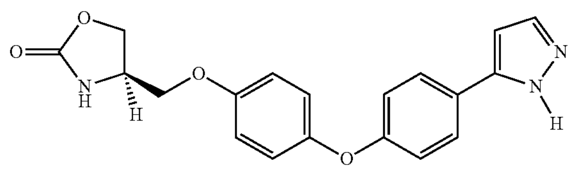 [SMILES: O=C1N[C@H](COc2ccc(Oc3ccc(-c4ccn[nH]4)cc3)cc2)CO1] | (4R)-4-({4-[4-(1H-pyrazol-5-yl)phenoxy]phenoxy}methyl)-1,3-oxazolidin-2-one |
| 13 | 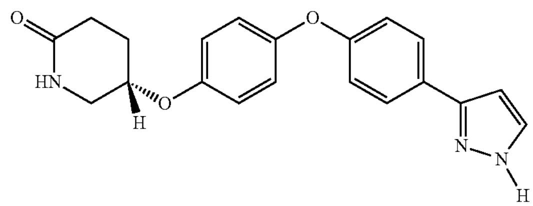 [SMILES: O=C1CC[C@H](Oc2ccc(Oc3ccc(-c4cc[nH]n4)cc3)cc2)CN1] | (5S)-5-{4-[4-(1H-pyrazol-3-yl)phenoxy]phenoxy}piperidin-2-one |
| 14 | 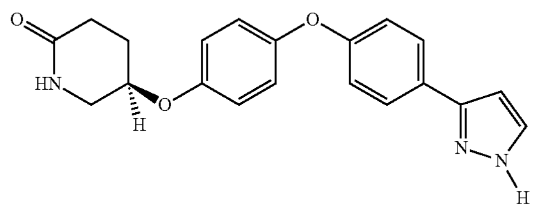 [SMILES: O=C1CC[C@@H](Oc2ccc(Oc3ccc(-c4cc[nH]n4)cc3)cc2)CN1] | (5R)-5-{4-[4-(1H-pyrazol-3-yl)phenoxy]phenoxy}piperidin-2-one |
| 15 | 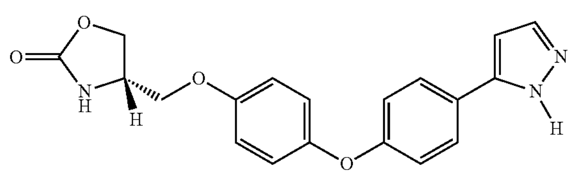 [SMILES: O=C1N[C@@H](COc2ccc(Oc3ccc(-c4ccn[nH]4)cc3)cc2)CO1] | (4S)-4-({4-[4-(1H-pyrazol-5-yl)phenoxy]phenoxy}methyl)-1,3-oxazolidin-2-one |
| 16 | 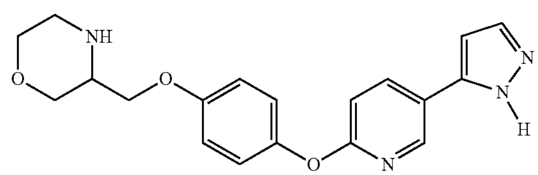 [SMILES: c1cc(-c2ccc(Oc3ccc(OCC4COCCN4)cc3)nc2)[nH]n1] | 3-[(4-{[5-(1H-pyrazol-5-yl)pyridin-2-yl]oxy}phenoxy)methyl]morpholine |
| 17 | 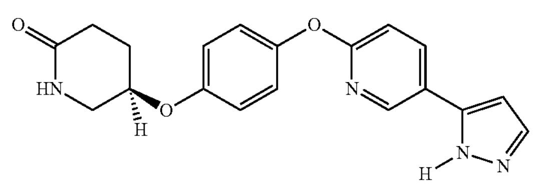 [SMILES: O=C1CC[C@@H](Oc2ccc(Oc3ccc(-c4ccn[nH]4)cn3)cc2)CN1] | (5R)-5-(4-{[5-(1H-pyrazol-5-yl)pyridin-2-yl]oxy}phenoxy)piperidin-2-one |
| 18 | 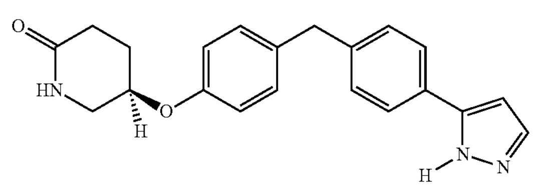 [SMILES: O=C1CC[C@@H](Oc2ccc(Cc3ccc(-c4ccn[nH]4)cc3)cc2)CN1] | (5R)-5-{4-[4-(1H-pyrazol-5-yl)benzyl]phenoxy}piperidin-2-one |
| 19 | 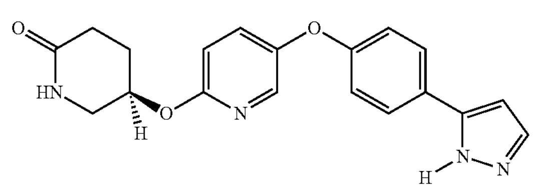 [SMILES: O=C1CC[C@@H](Oc2ccc(Oc3ccc(-c4ccn[nH]4)cc3)cn2)CN1] | (5R)-5-({5-[4-(1H-pyrazol-5-yl)phenoxy]pyridin-2-yl}oxy)piperidin-2-one |

TABLE 1-continued

Exemplary compounds of the invention.

| Ex. No. | Structure | Name |
|---|---|---|
| 20 | 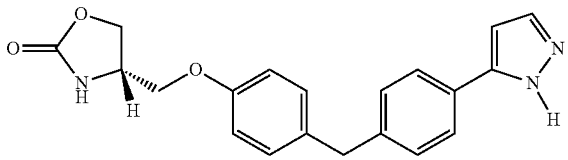 [SMILES: O=C1N[C@@H](COc2ccc(Cc3ccc(-c4ccn[nH]4)cc3)cc2)CO1] | (4S)-4-({4-[4-(1H-pyrazol-5-yl)benzyl]phenoxy}methyl)-1,3-oxazolidin-2-one |
| 21 | 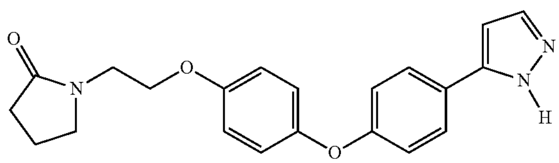 [SMILES: O=C1CCCN1CCOc1ccc(Oc2ccc(-c3ccn[nH]3)cc2)cc1] | 1-(2-{4-[4-(1H-pyrazol-5-yl)phenoxy]phenoxy}ethyl)pyrrolidin-2-one |
| 22 | 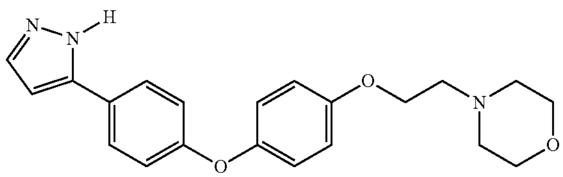 | 4-(2-{4-[4-(1H-pyrazol-5-yl)phenoxy]phenoxy}ethyl)morpholine |
| 23 | 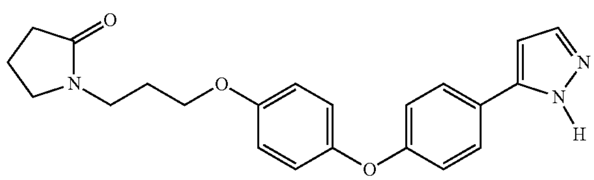 [SMILES: O=C1CCCN1CCCOc1ccc(Oc2ccc(-c3ccn[nH]3)cc2)cc1] | 1-(3-{4-[4-(1H-pyrazol-5-yl)phenoxy]phenoxy}propyl)pyrrolidin-2-one |
| 24 | 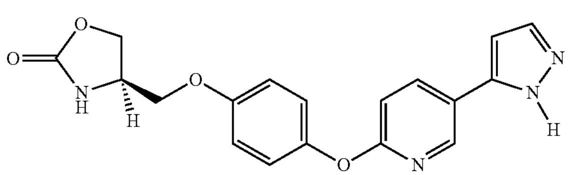 [SMILES: O=C1N[C@H](COc2ccc(Oc3ccc(-c4ccn[nH]4)cn3)cc2)CO1] | (4R)-4-[(4-{[5-(1H-pyrazol-5-yl)pyridin-2-yl]oxy}phenoxy)methyl]-1,3-oxazolidin-2-one |
| 25 | 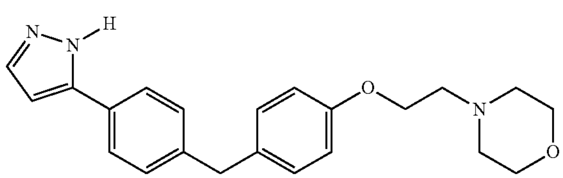 [SMILES: c1cc(-c2ccc(Cc3ccc(OCCN4CCOCC4)cc3)cc2)[nH]n1] | 4-(2-{4-[4-(1H-pyrazol-5-yl)benzyl]phenoxy}ethyl)morpholine |
| 26 | 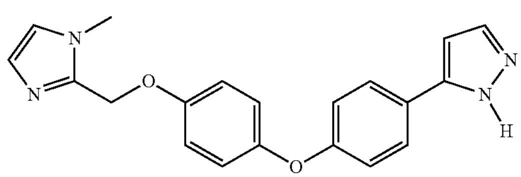 [SMILES: Cn1ccnc1COc1ccc(Oc2ccc(-c3ccn[nH]3)cc2)cc1] | 5-(4-{4-[(1-methyl-1H-imidazol-2-yl)methoxy]phenoxy}phenyl)-1H-pyrazole |
| 27 | 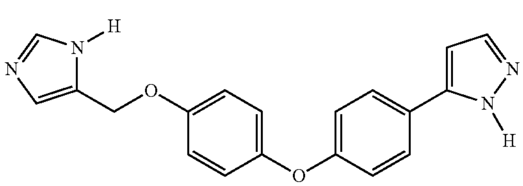 [SMILES: c1cc(-c2ccc(Oc3ccc(OCc4cnc[nH]4)cc3)cc2)[nH]n1] | 5-{4-[4-(1H-imidazol-5-ylmethoxy)phenoxy]phenyl}-1H-pyrazole |

TABLE 1-continued

Exemplary compounds of the invention.

| Ex. No. | Structure | Name |
|---|---|---|
| 28 | 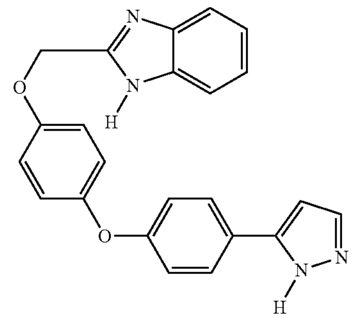 [SMILES: c1ccc2[nH]c(COc3ccc(Oc4ccc(-c5ccn[nH]5)cc4)cc3)nc2c1] | 2-({4-[4-(1H-pyrazol-5-yl)phenoxy]phenoxy}methyl)-1H-benzimidazole |
| 29 | 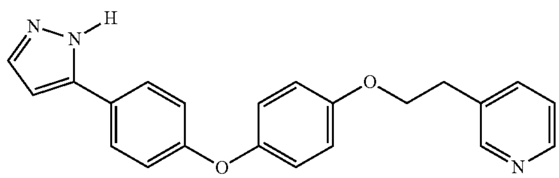 | 3-(2-{4-[4-(1H-pyrazol-5-yl)phenoxy]phenoxy}ethyl)pyridine |
| 30 | 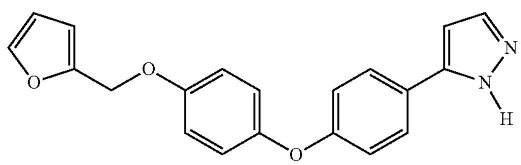 [SMILES: c1coc(COc2ccc(Oc3ccc(-c4ccn[nH]4)cc3)cc2)c1] | 5-{4-[4-(2-furylmethoxy)phenoxy]phenyl}-1H-pyrazole |
| 31 | 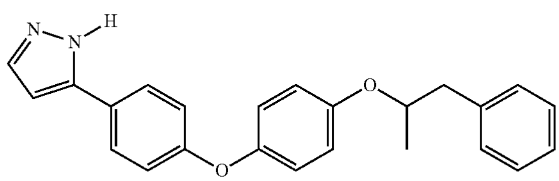 [SMILES: CC(Cc1ccccc1)Oc1ccc(Oc2ccc(-c3ccn[nH]3)cc2)cc1] | 5-{4-[4-(1-methyl-2-phenylethoxy)phenoxy]phenyl}-1H-pyrazole |
| 32 | 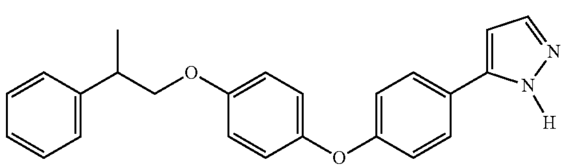 [SMILES: CC(COc1ccc(Oc2ccc(-c3ccn[nH]3)cc2)cc1)c1ccccc1] | 5-{4-[4-(2-phenylpropoxy)phenoxy]phenyl}-1H-pyrazole |
| 33 | 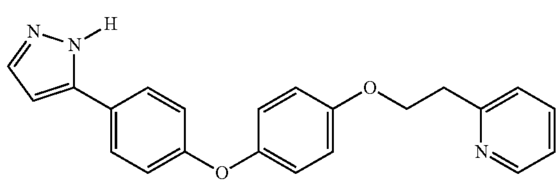 [SMILES: c1ccc(CCOc2ccc(Oc3ccc(-c4ccn[nH]4)cc3)cc2)nc1] | 2-(2-{4-[4-(1H-pyrazol-5-yl)phenoxy]phenoxy}ethyl)pyridine |
| 34 | 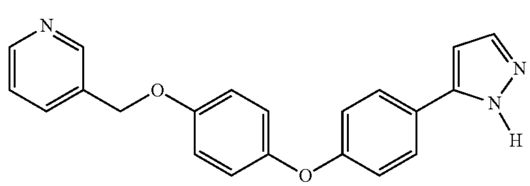 [SMILES: c1cncc(COc2ccc(Oc3ccc(-c4ccn[nH]4)cc3)cc2)c1] | 3-({4-[4-(1H-pyrazol-5-yl)phenoxy]phenoxy}methyl)pyridine |
| 35 | 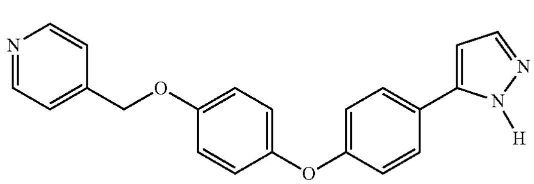 [SMILES: c1cc(COc2ccc(Oc3ccc(-c4ccn[nH]4)cc3)cc2)ccn1] | 4-({4-[4-(1H-pyrazol-5-yl)phenoxy]phenoxy}methyl)pyridine |

TABLE 1-continued

Exemplary compounds of the invention.

| Ex. No. | Structure | Name |
|---|---|---|
| 36 | 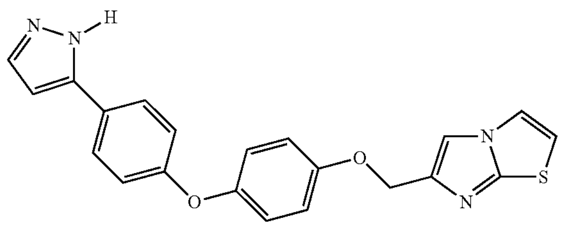 [SMILES: c1cc(-c2ccc(Oc3ccc(OCc4cn5ccsc5n4)cc3)cc2)[nH]n1] | 6-({4-[4-(1H-pyrazol-5-yl)phenoxy]phenoxy}methyl)imidazo[2,1-b][1,3]thiazole |
| 37 | 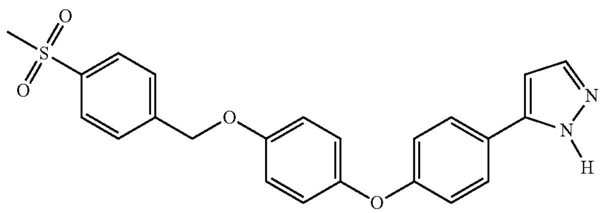 [SMILES: CS(=O)(=O)c1ccc(COc2ccc(Oc3ccc(-c4ccn[nH]4)cc3)cc2)cc1] | 5-[4-(4-{[4-(methylsulfonyl)benzyl]oxy}phenoxy)phenyl]-1H-pyrazole |
| 38 | 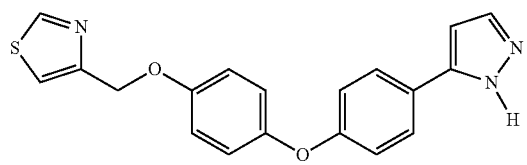 [SMILES: c1cc(-c2ccc(Oc3ccc(OCc4cscn4)cc3)cc2)[nH]n1] | 4-{4-[4-(2H-Pyrazol-3-yl)-phenoxy]-phenoxymethyl}-thiazole |
| 39 | 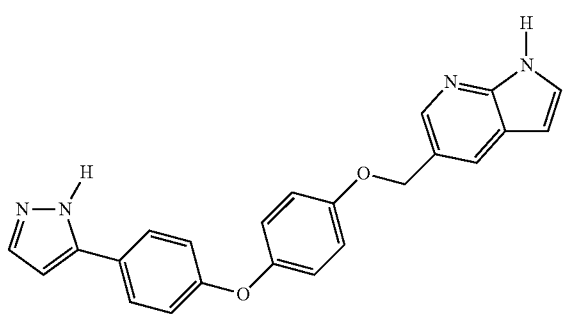 [SMILES: c1cc(-c2ccc(Oc3ccc(OCc4cnc5[nH]ccc5c4)cc3)cc2)[nH]n1] | 5-({4-[4-(1H-pyrazol-5-yl)phenoxy]phenoxy}methyl)-1H-pyrrolo[2,3-b]pyridine |
| 40 | 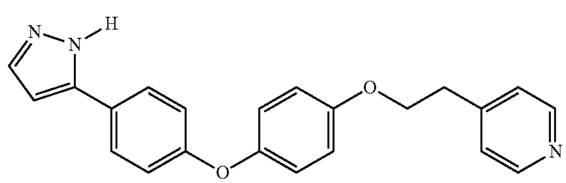 [SMILES: c1cc(CCOc2ccc(Oc3ccc(-c4ccn[nH]4)cc3)cc2)ccn1] | 4-(2-{4-[4-(1H-pyrazol-5-yl)phenoxy]phenoxy}ethyl)pyridine |
| 41 | 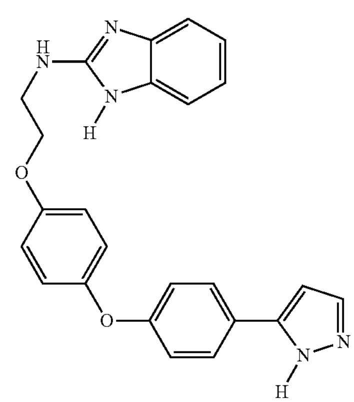 [SMILES: c1ccc2[nH]c(NCCOc3ccc(Oc4ccc(-c5ccn[nH]5)cc4)cc3)nc2c1] | N-(2-{4-[4-(1H-pyrazol-5-yl)phenoxy]phenoxy}ethyl)-1H-benzimidazol-2-amine |

TABLE 1-continued

Exemplary compounds of the invention.

| Ex. No. | Structure | Name |
|---|---|---|
| 42 | 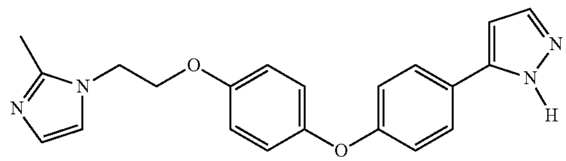 [SMILES: Cc1nccn1CCOc1ccc(Oc2ccc(-c3ccn[nH]3)cc2)cc1] | 5-(4-{4-[2-(2-methyl-1H-imidazol-1-yl)ethoxy]phenoxy]phenyl)-1H-pyrazole |
| 43 | 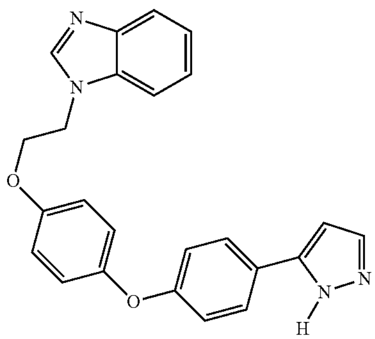 [SMILES: c1ccc2c(c1)ncn2CCOc1ccc(Oc2ccc(-c3ccn[nH]3)cc2)cc1] | 1-(2-{4-[4-(1H-pyrazol-5-yl)phenoxy]phenoxy}ethyl)-1H-benzimidazole |
| 44 | 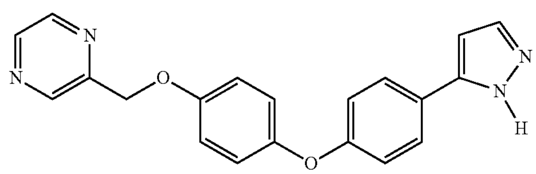 [SMILES: c1cnc(COc2ccc(Oc3ccc(-c4ccn[nH]4)cc3)cc2)cn1] | 2-({4-[4-(1H-pyrazol-5-yl)phenoxy]phenoxy}methyl)pyrazine |
| 45 | 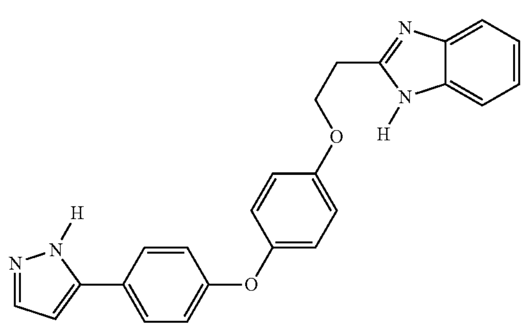 [SMILES: c1ccc2[nH]c(CCOc3ccc(Oc4ccc(-c5ccn[nH]5)cc4)cc3)nc2c1] | 2-(2-{4-[4-(1H-pyrazol-5-yl)phenoxy]phenoxy}ethyl)-1H-benzimidazole |
| 46 | 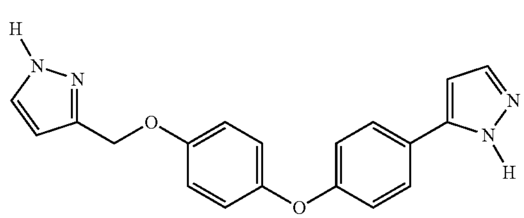 [SMILES: c1cc(-c2ccc(Oc3ccc(OCc4cc[nH]n4)cc3)cc2)[nH]n1] | 3-({4-[4-(1H-pyrazol-5-yl)phenoxy]phenoxy}methyl)-1H-pyrazole |

TABLE 1-continued

Exemplary compounds of the invention.

| Ex. No. | Structure | Name |
|---|---|---|
| 47 | 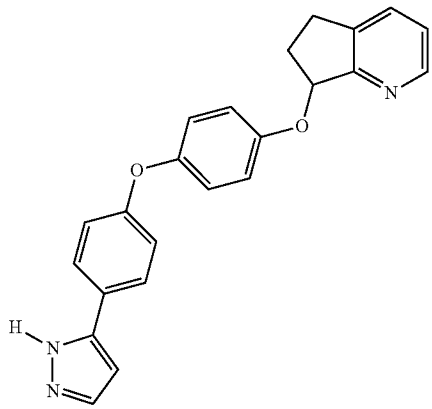 [SMILES: c1cnc2c(c1)CCC2Oc1ccc(Oc2ccc(-c3ccn[nH]3)cc2)cc1] | 7-{4-[4-(1H-pyrazol-5-yl)phenoxy]phenoxy}-6,7-dihydro-5H-cyclopenta[b]pyridine |
| 48 | 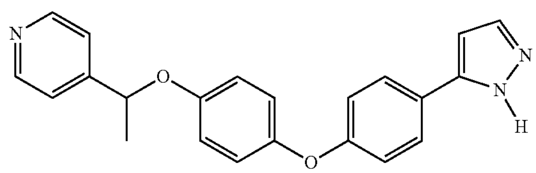 [SMILES: CC(Oc1ccc(Oc2ccc(-c3ccn[nH]3)cc2)cc1)c1ccncc1] | 4-(1-{4-[4-(1H-pyrazol-5-yl)phenoxy]phenoxy}ethyl)pyridine |
| 49 | 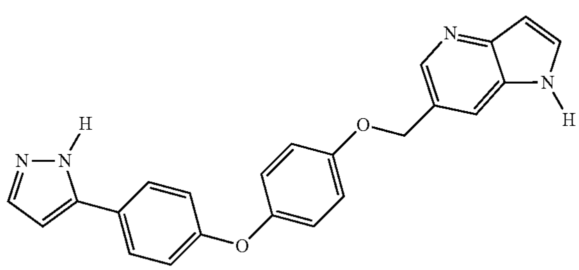 [SMILES: c1cc(-c2ccc(Oc3ccc(OCc4cnc5cc[nH]c5c4)cc3)cc2)[nH]n1] | 6-({4-[4-(1H-pyrazol-5-yl)phenoxy]phenoxy}methyl)-1H-pyrrolo[3,2-b]pyridine |
| 50 | 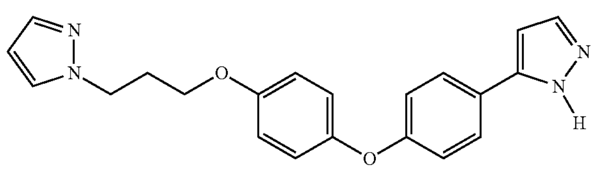 [SMILES: c1cnn(CCCOc2ccc(Oc3ccc(-c4ccn[nH]4)cc3)cc2)c1] | 1-(3-{4-[4-(1H-pyrazol-5-yl)phenoxy]phenoxy}propyl)-1H-pyrazole |
| 51 | 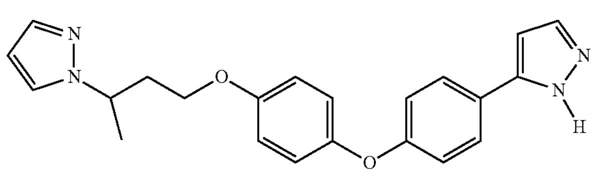 [SMILES: CC(CCOc1ccc(Oc2ccc(-c3ccn[nH]3)cc2)cc1)n1cccn1] | 1-(1-methyl-3-{4-[4-(1H-pyrazol-5-yl)phenoxy]phenoxy}propyl)-1H-pyrazole |
| 52 | 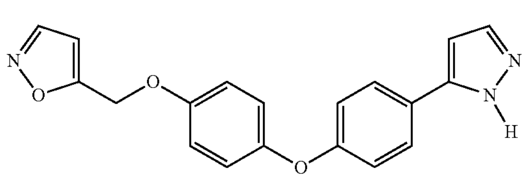 [SMILES: c1cc(-c2ccc(Oc3ccc(OCc4ccno4)cc3)cc2)[nH]n1] | 5-({4-[4-(1H-pyrazol-5-yl)phenoxy]phenoxy}methyl)isoxazole |

TABLE 1-continued

Exemplary compounds of the invention.

| Ex. No. | Structure | Name |
|---|---|---|
| 53 | 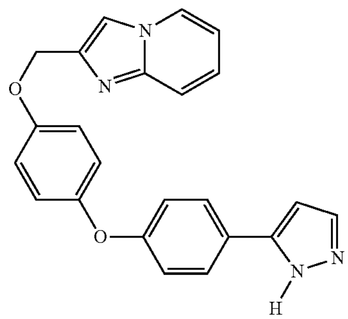 [SMILES: c1ccn2cc(COc3ccc(Oc4ccc(-c5ccn[nH]5)cc4)cc3)nc2c1] | 2-({4-[4-(1H-pyrazol-5-yl)phenoxy]phenoxy}methyl)imidazo[1,2-a]pyridine |
| 54 | 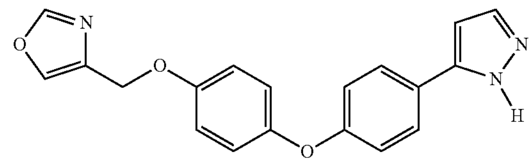 [SMILES: c1cc(-c2ccc(Oc3ccc(OCc4cocn4)cc3)cc2)[nH]n1] | 4-({4-[4-(1H-pyrazol-5-yl)phenoxy]phenoxy}methyl)-1,3-oxazole |
| 55 | 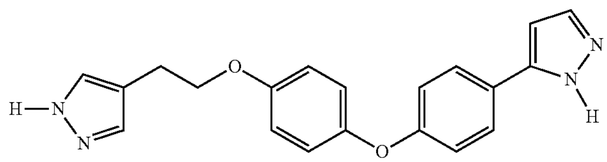 [SMILES: c1cc(-c2ccc(Oc3ccc(OCCc4cn[nH]c4)cc3)cc2)[nH]n1] | 4-(2-{4-[4-(1H-pyrazol-5-yl)phenoxy]phenoxy}ethyl)-1H-pyrazole |
| 56 | 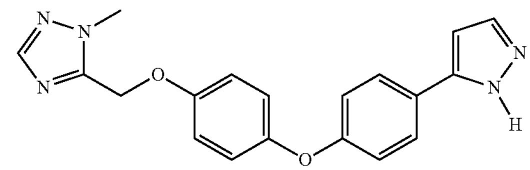 [SMILES: Cn1ncnc1COc1ccc(Oc2ccc(-c3ccn[nH]3)cc2)cc1] | 1-methyl-5-({4-[4-(1H-pyrazol-5-yl)phenoxy]phenoxy}methyl)-1H-1,2,4-triazole |
| 57 | 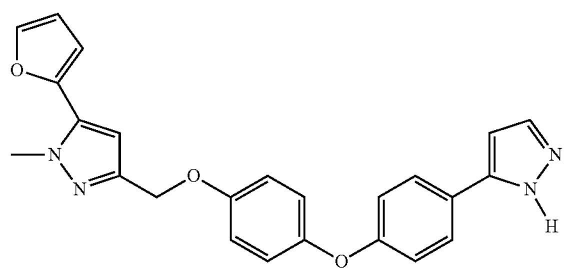 [SMILES: Cn1nc(COc2ccc(Oc3ccc(-c4ccn[nH]4)cc3)cc2)cc1-c1ccco1] | 5-(2-furyl)-1-methyl-3-({4-[4-(1H-pyrazol-5-yl)phenoxy]phenoxy}methyl)-1H-pyrazole |
| 58 | 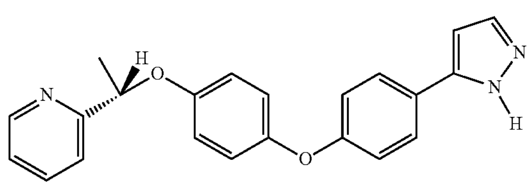 [SMILES: C[C@@H](Oc1ccc(Oc2ccc(-c3ccn[nH]3)cc2)cc1)c1ccccn1] | 2-[(1S)-1-{4-[4-(1H-pyrazol-5-yl)phenoxy]phenoxy}ethyl]pyridine |
| 59 | 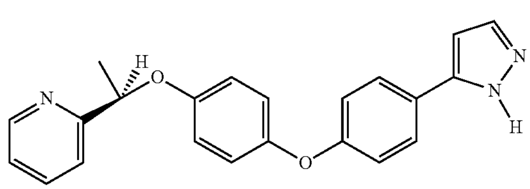 [SMILES: C[C@H](Oc1ccc(Oc2ccc(-c3ccn[nH]3)cc2)cc1)c1ccccn1] | 2-[(1R)-1-{4-[4-(1H-pyrazol-5-yl)phenoxy]phenoxy}ethyl]pyridine |

TABLE 1-continued

Exemplary compounds of the invention.

| Ex. No. | Structure | Name |
|---|---|---|
| 60 | 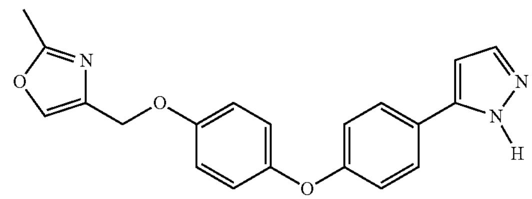 [SMILES: Cc1nc(COc2ccc(Oc3ccc(-c4ccn[nH]4)cc3)cc2)co1] | 2-methyl-4-({4-[4-(1H-pyrazol-5-yl)phenoxy]phenoxy}methyl)-1,3-oxazole |
| 61 | 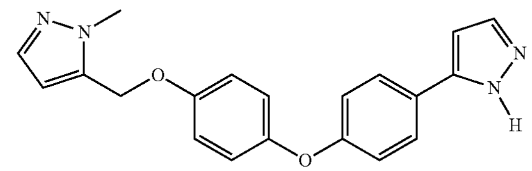 [SMILES: Cn1nccc1COc1ccc(Oc2ccc(-c3ccn[nH]3)cc2)cc1] | 1-methyl-5-({4-[4-(1H-pyrazol-5-yl)phenoxy]phenoxy}methyl)-1H-pyrazole |
| 62 | 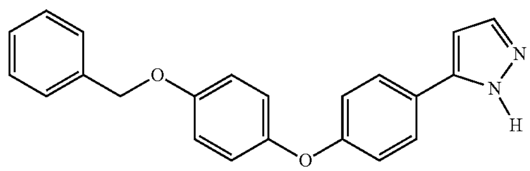 [SMILES: c1ccc(COc2ccc(Oc3ccc(-c4ccn[nH]4)cc3)cc2)cc1] | 5-{4-[4-(benzyloxy)phenoxy]phenyl}-1H-pyrazole |
| 63 | 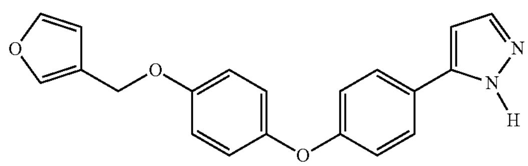 [SMILES: c1cc(-c2ccc(Oc3ccc(OCc4ccoc4)cc3)cc2)[nH]n1] | 5-{4-[4-(3-furylmethoxy)phenoxy]phenyl}-1H-pyrazole |
| 64 | 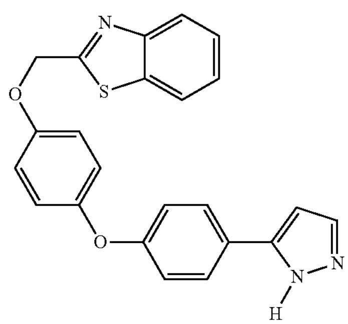 [SMILES: c1ccc2sc(COc3ccc(Oc4ccc(-c5ccn[nH]5)cc4)cc3)nc2c1] | 2-({4-[4-(1H-pyrazol-5-yl)phenoxy]phenoxy}methyl)-1,3-benzothiazole |
| 65 | 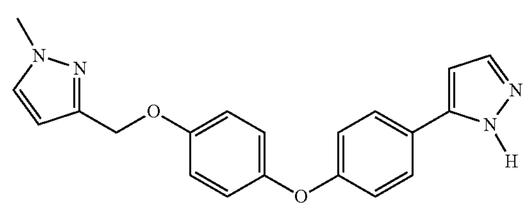 [SMILES: Cn1ccc(COc2ccc(Oc3ccc(-c4ccn[nH]4)cc3)cc2)n1] | 1-methyl-3-({4-[4-(1H-pyrazol-5-yl)phenoxy]phenoxy}methyl)-1H-pyrazole |
| 66 | 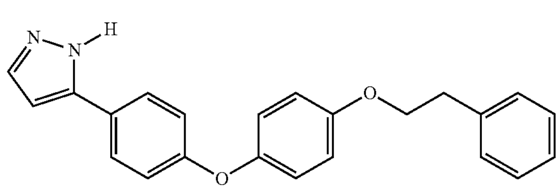 [SMILES: c1ccc(CCOc2ccc(Oc3ccc(-c4ccn[nH]4)cc3)cc2)cc1] | 5-{4-[4-(2-phenylethoxy)phenoxy]phenyl}-1H-pyrazole |

TABLE 1-continued

Exemplary compounds of the invention.

| Ex. No. | Structure | Name |
|---|---|---|
| 67 | 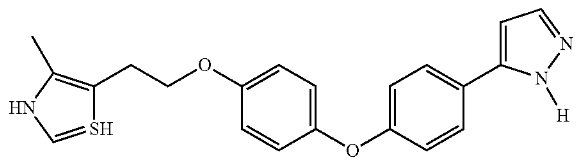 | 4-Methyl-5-(2-{4-[4-(2H-pyrazol-3-yl)-phenoxy]-phenoxy}-ethyl)-thiazole |
| 68 | 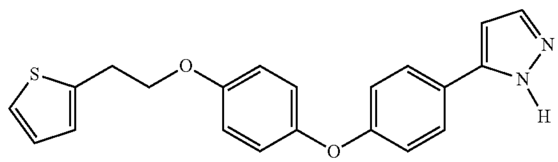 [SMILES: c1csc(CCOc2ccc(Oc3ccc(-c4ccn[nH]4)cc3)cc2)c1] | 5-(4-{4-[2-(2-thienyl)ethoxy]phenoxy}phenyl)-1H-pyrazole |
| 69 | 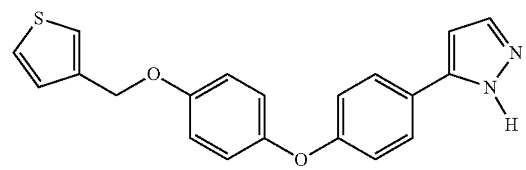 [SMILES: c1cc(-c2ccc(Oc3ccc(OCc4ccsc4)cc3)cc2)[nH]n1] | 5-{4-[4-(3-thienylmethoxy)phenoxy]phenyl}-1H-pyrazole |
| 70 | 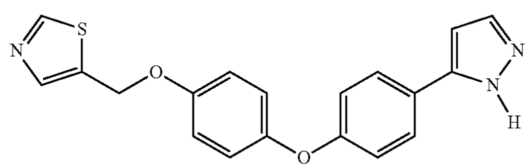 [SMILES: c1cc(-c2ccc(Oc3ccc(OCc4cncs4)cc3)cc2)[nH]n1] | 5-({4-[4-(1H-pyrazol-5-yl)phenoxy]phenoxy}methyl)-1,3-thiazole |
| 71 | 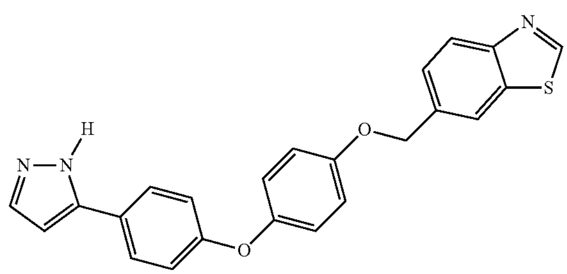 [SMILES: c1cc(-c2ccc(Oc3ccc(OCc4ccc5ncsc5c4)cc3)cc2)[nH]n1] | 6-({4-[4-(1H-pyrazol-5-yl)phenoxy]phenoxy}methyl)-1,3-benzothiazole |
| 72 | 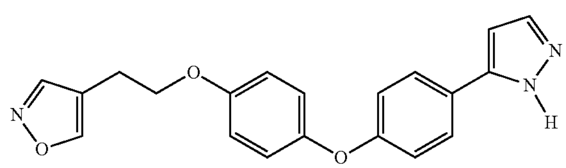 [SMILES: c1cc(-c2ccc(Oc3ccc(OCCc4cnoc4)cc3)cc2)[nH]n1] | 4-(2-{4-[4-(1H-pyrazol-5-yl)phenoxy]phenoxy}ethyl)isoxazole |
| 73 | 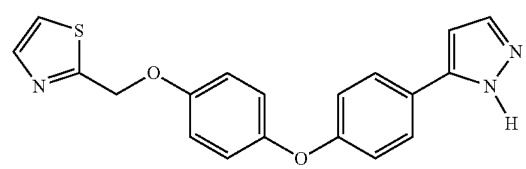 [SMILES: c1cc(-c2ccc(Oc3ccc(OCc4nccs4)cc3)cc2)[nH]n1] | 2-({4-[4-(1H-pyrazol-5-yl)phenoxy]phenoxy}methyl)-1,3-thiazole |
| 74 | 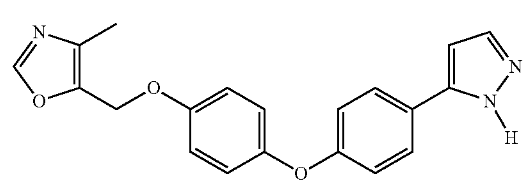 [SMILES: Cc1ncoc1COc1ccc(Oc2ccc(-c3ccn[nH]3)cc2)cc1] | 4-methyl-5-({4-[4-(1H-pyrazol-5-yl)phenoxy]phenoxy}methyl)-1,3-oxazole |

TABLE 1-continued

Exemplary compounds of the invention.

| Ex. No. | Structure | Name |
|---|---|---|
| 75 | 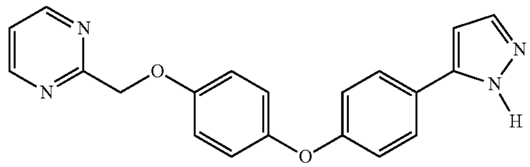 [SMILES: c1cnc(COc2ccc(Oc3ccc(-c4ccn[nH]4)cc3)cc2)nc1] | 2-({4-[4-(1H-pyrazol-5-yl)phenoxy]phenoxy}methyl)pyrimidine |
| 76 | 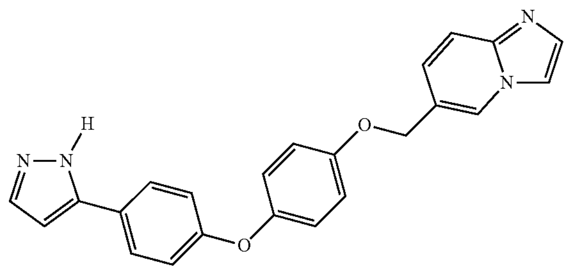 [SMILES: c1cc(-c2ccc(Oc3ccc(OCc4ccc5nccn5c4)cc3)cc2)[nH]n1] | 6-({4-[4-(1H-pyrazol-5-yl)phenoxy]phenoxy}methyl)imidazo[1,2-a]pyridine |
| 77 | 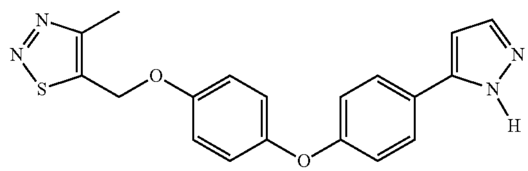 [SMILES: Cc1nnsc1COc1ccc(Oc2ccc(-c3ccn[nH]3)cc2)cc1] | 4-Methyl-5-{4-[4-(2H-pyrazol-3-yl)-phenoxy]-phenoxymethyl}-[1,2,3]thiadiazole |
| 78 | 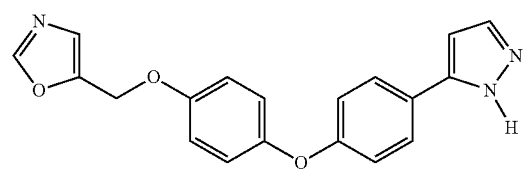 [SMILES: c1cc(-c2ccc(Oc3ccc(OCc4cnco4)cc3)cc2)[nH]n1] | 5-({4-[4-(1H-pyrazol-5-yl)phenoxy]phenoxy}methyl)-1,3-oxazole |
| 79 | 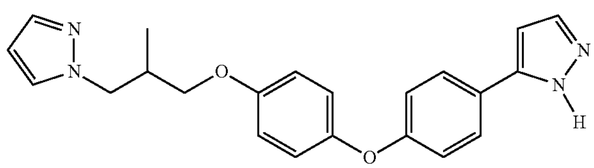 [SMILES: CC(COc1ccc(Oc2ccc(-c3ccn[nH]3)cc2)cc1)Cn1cccn1] | 1-(2-methyl-3-{4-[4-(1H-pyrazol-5-yl)phenoxy]phenoxy}propyl)-1H-pyrazole |
| 80 | 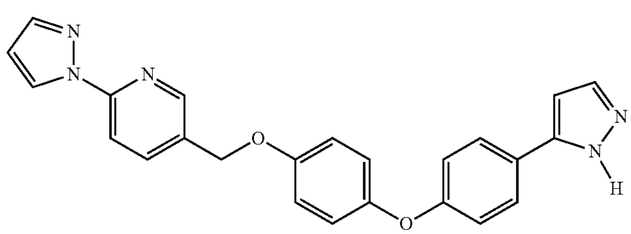 [SMILES: c1cnn(-c2ccc(COc3ccc(Oc4ccc(-c5ccn[nH]5)cc4)cc3)cn2)c1] | 2-(1H-pyrazol-1-yl)-5-({4-[4-(1H-pyrazol-5-yl)phenoxy]phenoxy}methyl)pyridine |
| 81 | 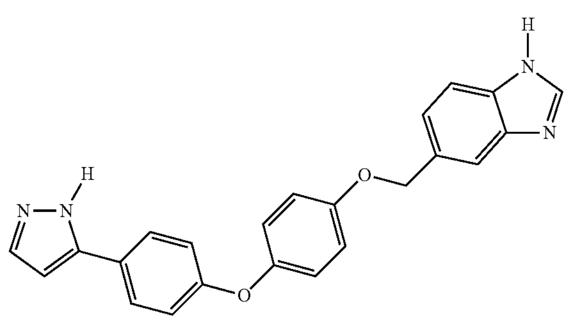 [SMILES: c1cc(-c2ccc(Oc3ccc(OCc4ccc5[nH]cnc5c4)cc3)cc2)[nH]n1] | 5-({4-[4-(1H-pyrazol-5-yl)phenoxy]phenoxy}methyl)-1H-benzimidazole |

TABLE 1-continued

Exemplary compounds of the invention.

| Ex. No. | Structure | Name |
|---|---|---|
| 82 | 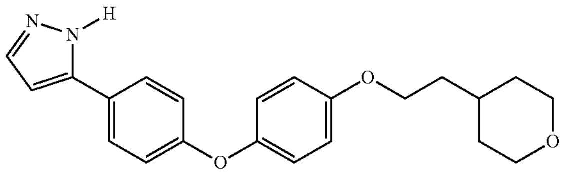 [SMILES: c1cc(-c2ccc(Oc3ccc(OCCC4CCOCC4)cc3)cc2)[nH]n1] | 5-(4-{4-[2-(tetrahydro-2H-pyran-4-yl)ethoxy]phenoxy}phenyl)-1H-pyrazole |
| 83 | 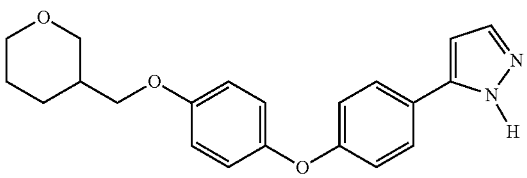 [SMILES: c1cc(-c2ccc(Oc3ccc(OCC4CCCOC4)cc3)cc2)[nH]n1] | 5-{4-[4-(tetrahydro-2H-pyran-3-ylmethoxy)phenoxy]phenyl}-1H-pyrazole |
| 84 | 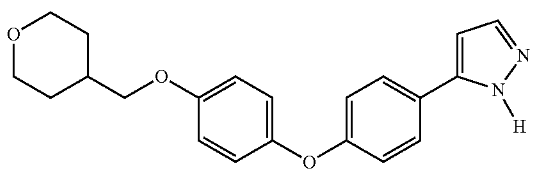 [SMILES: c1cc(-c2ccc(Oc3ccc(OCC4CCOCC4)cc3)cc2)[nH]n1] | 5-{4-[4-(tetrahydro-2H-pyran-4-ylmethoxy)phenoxy]phenyl}-1H-pyrazole |
| 85 | 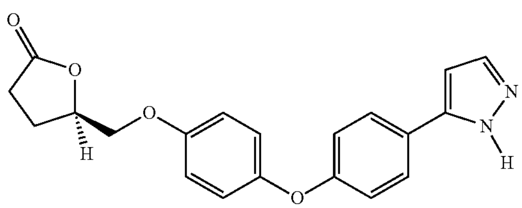 [SMILES: O=C1CC[C@H](COc2ccc(Oc3ccc(-c4ccn[nH]4)cc3)cc2)O1] | (5R)-5-({4-[4-(1H-pyrazol-5-yl)phenoxy]phenoxy}methyl)dihydrofuran-2(3H)-one |
| 86 | 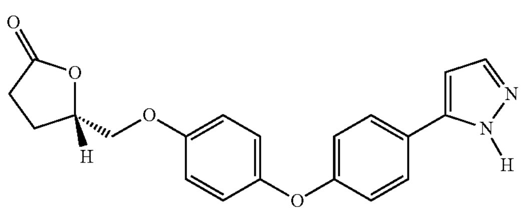 [SMILES: O=C1CC[C@@H](COc2ccc(Oc3ccc(-c4ccn[nH]4)cc3)cc2)O1] | (5S)-5-({4-[4-(1H-pyrazol-5-yl)phenoxy]phenoxy}methyl)dihydrofuran-2(3H)-one |
| 87 | 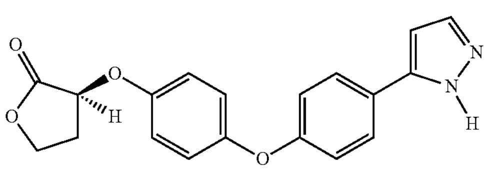 [SMILES: O=C1OCC[C@@H]1Oc1ccc(Oc2ccc(-c3ccn[nH]3)cc2)cc1] | (3S)-3-{4-[4-(1H-pyrazol-5-yl)phenoxy]phenoxy}dihydrofuran-2(3H)-one |
| 88 | 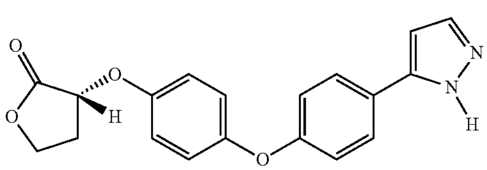 [SMILES: O=C1OCC[C@H]1Oc1ccc(Oc2ccc(-c3ccn[nH]3)cc2)cc1] | (3R)-3-{4-[4-(1H-pyrazol-5-yl)phenoxy]phenoxy}dihydrofuran-2(3H)-one |
| 89 | 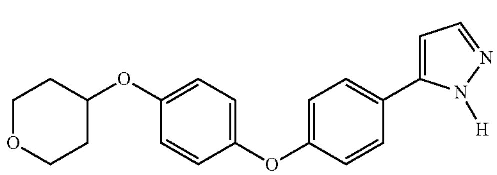 [SMILES: c1cc(-c2ccc(Oc3ccc(OC4CCOCC4)cc3)cc2)[nH]n1] | 5-{4-[4-(tetrahydro-2H-pyran-4-yloxy)phenoxy]phenyl}-1H-pyrazole |

TABLE 1-continued

Exemplary compounds of the invention.

| Ex. No. | Structure | Name |
|---|---|---|
| 90 | 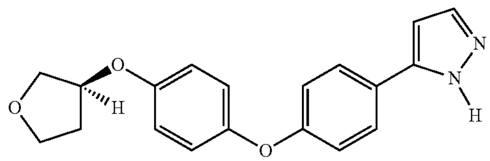 [SMILES: c1cc(-c2ccc(Oc3ccc(O[C@H]4CCOC4)cc3)cc2)[nH]n1] | 5-(4-{4-[(3S)-tetrahydrofuran-3-yloxy]phenoxy}phenyl)-1H-pyrazole |
| 91 | 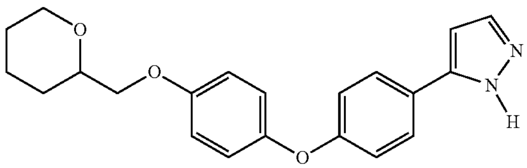 [SMILES: c1cc(-c2ccc(Oc3ccc(OCC4CCCCO4)cc3)cc2)[nH]n1] | 5-{4-[4-(tetrahydro-2H-pyran-2-ylmethoxy)phenoxy]phenyl}-1H-pyrazole |
| 92 | 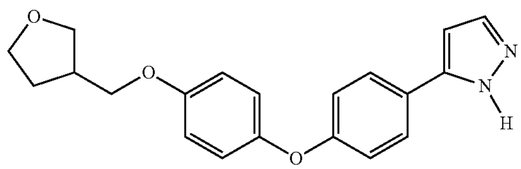 [SMILES: c1cc(-c2ccc(Oc3ccc(OCC4CCOC4)cc3)cc2)[nH]n1] | 5-{4-[4-(tetrahydrofuran-3-ylmethoxy)phenoxy]phenyl}-1H-pyrazole |
| 93 | 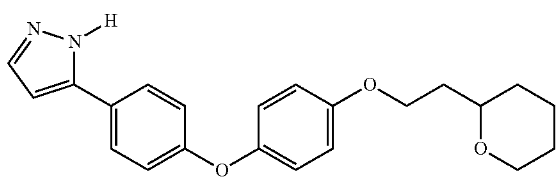 [SMILES: c1cc(-c2ccc(Oc3ccc(OCCC4CCCCO4)cc3)cc2)[nH]n1] | 5-(4-{4-[2-(tetrahydro-2H-pyran-2-yl)ethoxy]phenoxy}phenyl)-1H-pyrazole |
| 94 | 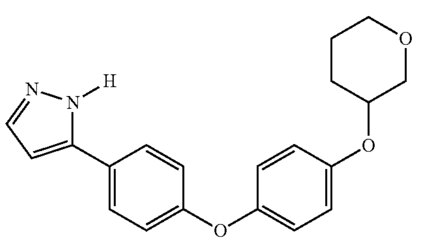 [SMILES: c1cc(-c2ccc(Oc3ccc(OC4CCCOC4)cc3)cc2)[nH]n1] | 5-{4-[4-(tetrahydro-2H-pyran-3-yloxy)phenoxy]phenyl}-1H-pyrazole |
| 95 | 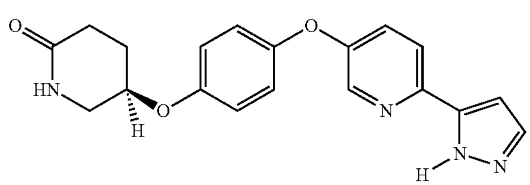 [SMILES: O=C1CC[C@@H](Oc2ccc(Oc3ccc(-c4ccn[nH]4)nc3)cc2)CN1] | (5R)-5-(4-{[6-(1H-pyrazol-5-yl)pyridin-3-yl]oxy}phenoxy)piperidin-2-one |

In one embodiment, the invention relates to any of the compounds depicted in Table 1, mixtures thereof, and pharmaceutically acceptable salts thereof.

In another embodiment, the invention relates to a compound selected from the group consisting of:
(4R)-4-({4-[4-(1H-pyrazol-5-yl)phenoxy]phenoxy}methyl)-1,3-oxazolidin-2-one;
(5R)-5-({4-[4-(1H-pyrazol-5-yl)phenoxy]phenoxy}methyl)pyrrolidin-2-one;
(5S)-5-({4-[4-(1H-pyrazol-5-yl)phenoxy]phenoxy}methyl)pyrrolidin-2-one;
(5S)-5-[(4-{[5-(1H-pyrazol-5-yl)pyridin-2-yl]oxy}-phenoxy)methyl]pyrrolidin-2-one;
4-({4-[4-(1H-pyrazol-5-yl)phenoxy]phenoxy}methyl)-1,3-oxazolidin-2-one;
3-[(4-{[5-(1H-pyrazol-5-yl)pyridin-2-yl]oxy}-phenoxy)methyl]morpholine;
4-(2-{4-[4-(1H-pyrazol-5-yl)phenoxy]phenoxy}ethyl)morpholine;
(4R)-4-[(4-{[5-(1H-pyrazol-5-yl)pyridin-2-yl]oxy}-phenoxy)methyl]-1,3-oxazolidin-2-one;
N-(2-{4-[4-(1H-pyrazol-5-yl)phenoxy]phenoxy}ethyl)-1H-benzimidazol-2-amine;
(5R)-5-{4-[4-(1H-pyrazol-3-yl)phenoxy]phenoxy}piperidin-2-one;
(4S)-4-({4-[4-(1H-pyrazol-5-yl)phenoxy]phenoxy}methyl)-1,3-oxazolidin-2-one;
5-(4-{4-[2-(2-methyl-1H-imidazol-1-yl)ethoxy]phenoxy}phenyl)-1H-pyrazole;
1-methyl-4-({4-[4-(1H-pyrazol-5-yl)phenoxy]phenoxy}methyl)pyrrolidin-2-one;
5-{4-[4-(1H-pyrazol-5-yl)phenoxy]phenoxy}piperidin-2-one;

(5S)-5-{4-[4-(1H-pyrazol-3-yl)phenoxy]phenoxy}piperidin-2-one;
4-(2-{4-[4-(1H-pyrazol-5-yl)benzyl]phenoxy}ethyl)morpholine;
(4S)-4-({4-[4-(1H-pyrazol-5-yl)benzyl]phenoxy}methyl)-1,3-oxazolidin-2-one;
1-methyl-5-({4-[4-(1H-pyrazol-5-yl)phenoxy]phenoxy}methyl)-1H-1,2,4-triazole;
1-(2-{4-[4-(1H-pyrazol-5-yl)phenoxy]phenoxy}ethyl)pyrrolidin-2-one;
1-(3-{4-[4-(1H-pyrazol-5-yl)phenoxy]phenoxy}propyl)pyrrolidin-2-one;
(5R)-5-{4-[4-(1H-pyrazol-5-yl)benzyl]phenoxy}piperidin-2-one;
mixtures thereof, and pharmaceutically acceptable salts thereof.

In another embodiment, the invention relates to a compound selected from the group consisting of:
3-[(4-{[5-(1H-pyrazol-5-yl)pyridin-2-yl]oxy}-phenoxy)methyl]morpholine;
(4R)-4-({4-[4-(1H-pyrazol-5-yl)phenoxy]phenoxy}methyl)-1,3-oxazolidin-2-one;
(4R)-4-[(4-{[5-(1H-pyrazol-5-yl)pyridin-2-yl]oxy}phenoxy)methyl]-1,3-oxazolidin-2-one;
4-(2-{4-[4-(1H-pyrazol-5-yl)benzyl]phenoxy}ethyl)morpholine;
4-({4-[4-(1H-pyrazol-5-yl)phenoxy]phenoxy}methyl)-1,3-oxazolidin-2-one;
(5S)-5-[(4-{[5-(1H-pyrazol-5-yl)pyridin-2-yl]oxy}-phenoxy)methyl]pyrrolidin-2-one;
(4S)-4-({4-[4-(1H-pyrazol-5-yl)phenoxy]phenoxy}methyl)-1,3-oxazolidin-2-one;
(5S)-5-({4-[4-(1H-pyrazol-5-yl)phenoxy]phenoxy}methyl)pyrrolidin-2-one;
5-(4-{4-[2-(2-methyl-1H-imidazol-1-yl)ethoxy]phenoxy}phenyl)-1H-pyrazole;
(5R)-5-{4-[4-(1H-pyrazol-3-yl)phenoxy]phenoxy}piperidin-2-one;
4-(2-{4-[4-(1H-pyrazol-5-yl)phenoxy]phenoxy}ethyl)morpholine;
(5S)-5-{4-[4-(1H-pyrazol-3-yl)phenoxy]phenoxy}piperidin-2-one;
5-{4-[4-(1H-pyrazol-5-yl)phenoxy]phenoxy}piperidin-2-one;
(4S)-4-({4-[4-(1H-pyrazol-5-yl)benzyl]phenoxy}methyl)-1,3-oxazolidin-2-one;
(5R)-5-({4-[4-(1H-pyrazol-5-yl)phenoxy]phenoxy}methyl)pyrrolidin-2-one;
1-methyl-4-({4-[4-(1H-pyrazol-5-yl)phenoxy]phenoxy}methyl)pyrrolidin-2-one;
(5R)-5-(4-{[6-(1H-pyrazol-5-yl)pyridin-3-yl]oxy}phenoxy)piperidin-2-one;
(5R)-5-(4-{[5-(1H-pyrazol-5-yl)pyridin-2-yl]oxy}phenoxy)piperidin-2-one;
1-(3-{4-[4-(1H-pyrazol-5-yl)phenoxy]phenoxy}propyl)pyrrolidin-2-one;
(5R)-5-({5-[4-(1H-pyrazol-5-yl)phenoxy]pyridin-2-yl}oxy)piperidin-2-one;
5-({4-[4-(1H-pyrazol-5-yl)phenoxy]phenoxy}methyl)-1,3-oxazolidin-2-one;
(5R)-5-{4-[4-(1H-pyrazol-5-yl)benzyl]phenoxy}piperidin-2-one;
N-(2-{4-[4-(1H-pyrazol-5-yl)phenoxy]phenoxy}ethyl)-1H-benzimidazol-2-amine;
2-({4-[4-(1H-pyrazol-5-yl)phenoxy]phenoxy}methyl)pyrazine;
5-(4-{4-[(3S)-tetrahydrofuran-3-yloxy]phenoxy}phenyl)-1H-pyrazole;
1-(2-{4-[4-(1H-pyrazol-5-yl)phenoxy]phenoxy}ethyl)pyrrolidin-2-one;
5-(4-{4-[(3R)-tetrahydrofuran-3-yloxy]phenoxy}phenyl)-1H-pyrazole;
(5S)-5-({5-[4-(1H-pyrazol-5-yl)phenoxy]pyridin-2-yl}oxy)piperidin-2-one;
1-methyl-5-({4-[4-(1H-pyrazol-5-yl)phenoxy]phenoxy}methyl)-1H-pyrazole;
5-{4-[4-(tetrahydrofuran-3-ylmethoxy)phenoxy]phenyl}-1H-pyrazole;
5-{4-[4-(tetrahydrofuran-2-ylmethoxy)phenoxy]phenyl}-1H-pyrazole;
6-({4-[4-(1H-pyrazol-5-yl)phenoxy]phenoxy}methyl)imidazo[1,2-a]pyridine;
5-{4-[4-(tetrahydro-2H-pyran-4-ylmethoxy)phenoxy]phenyl}-1H-pyrazole;
2-(1H-pyrazol-1-yl)-5-({4-[4-(1H-pyrazol-5-yl)phenoxy]phenoxy}methyl)pyridine;
5-({4-[4-(1H-pyrazol-5-yl)phenoxy]phenoxy}methyl)-1,3-oxazole; and
mixtures thereof, and pharmaceutically acceptable salts thereof.

In another embodiment, the invention relates to pharmaceutical compositions comprising one or more compounds of formula (I) as defined in any of the embodiment above, or a pharmaceutically acceptable salt thereof, and a pharmaceutically acceptable carrier or excipient.

Unless otherwise stated, all terms as used herein in this specification shall be understood to have their ordinary meaning as known in the art. Other more specific definitions are as follows:

The term "$(C_1\text{-}C_6)$alkyl" refers to branched and unbranched alkyl groups having from 1 to 6 carbon atoms. Examples of —$(C_1\text{-}C_6)$alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the $(C_1\text{-}C_6)$alkyl group can be the point of attachment to another group or moiety.

The term "—$(C_1\text{-}C_6)$alkylene-" refers to branched and unbranched alkyl linkers having from 1 to 6 carbon atoms. Examples of —$(C_1\text{-}C_6)$alkylene—include methylene, ethylene, propylene, butylene, pentylene, and hexylene.

The term "$(C_3\text{-}C_6)$cycloalkyl" refers to a nonaromatic 3- to 6-membered monocyclic carbocyclic radical. Examples of "$(C_3\text{-}C_6)$cycloalkyls" include cyclopropyl, cyclobutyl, cyclohexyl, cyclopentyl and cyclohexyl.

As used herein, the term "$(C_6\text{-}C_{10})$aryl" refers to an aromatic hydrocarbon rings containing from six to ten carbon ring and includes monocyclic rings and bicyclic rings where at least one of the rings is aromatic. Non-limiting examples of $C_{6\text{-}10}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "4 to 11-membered heterocycle" includes stable nonaromatic 4-8 member monocyclic heterocyclic radical or a stable nonaromatic 6 to 11-membered fused bicyclic, bridged bicyclic or spirocyclic heterocyclic radical. The 4 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 member monocyclic heterocyclic radicals include tetrahydrofuranyl, azetidinyl, pyrrolidinyl, pyranyl, tetrahydropyranyl, dioxanyl, thiomorpholinyl, 1,1-dioxo-1λ⁶-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. As used herein, the term "5 to 11-membered heteroaryl" includes aromatic 5 to 6-membered monocyclic heteroaryls and aromatic 7 to 11-membered heteroaryl bicyclic rings where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl.

It will be understood that when a heterocyclyl or heteroaryl contains a S ring atom, such S ring atom can be present in the ring in its divalent, tetravalent, or hexavalent form, i.e., —S—, —S(O)— or —S(O)₂—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "heteroatom" as used herein shall be understood to mean atoms other than carbon such as O, N, and S.

The term "halo" or "halogen" refers to fluoro, chloro, bromo or iodo.

The symbol

means point of attachment of a group R to a moiety.

In all alkyl groups or carbon chains one or more carbon atoms can be optionally replaced by heteroatoms O, S or N. It shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

For all compounds disclosed in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The compounds of the invention may contain one or more asymmetric carbon atoms and, therefore, may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

The compounds of the invention are only those which are contemplated to be "chemically stable" as will be appreciated by those skilled in the art. For example, a compound which would have a "dangling valency" or a "carbanion" is not a compound contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N(C₁-C₄ alkyl)₄⁺ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The compounds of the invention may be prepared by the methods described below in Schemes 1 and 2, where the groups $A^1$-$A^3$, $L^1$, $L^2$ and D are as defined above for the compound of formula (I) unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section.

Scheme 1 depicts a general synthetic procedure for making the compounds of formula (I) where $A^3$ is CH.

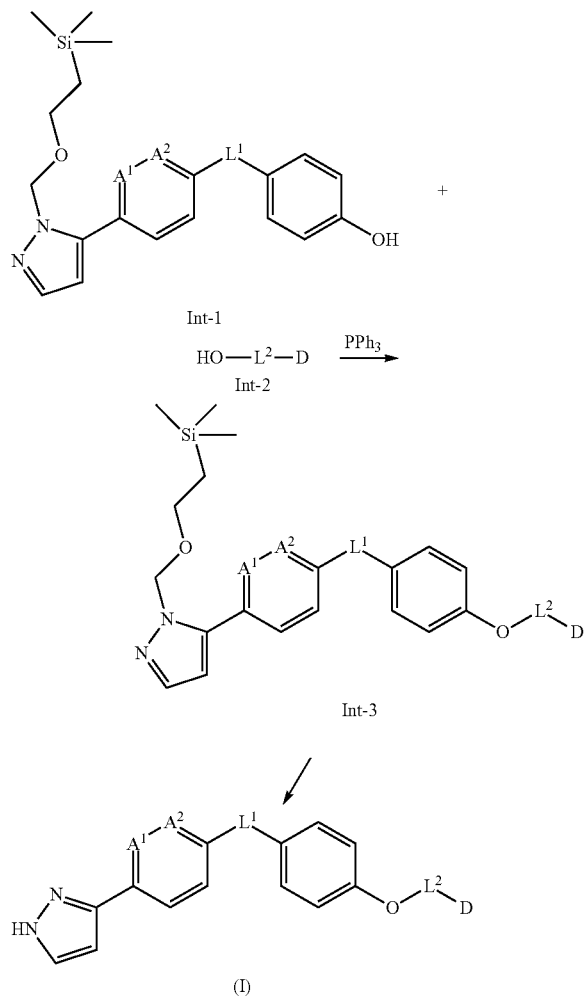

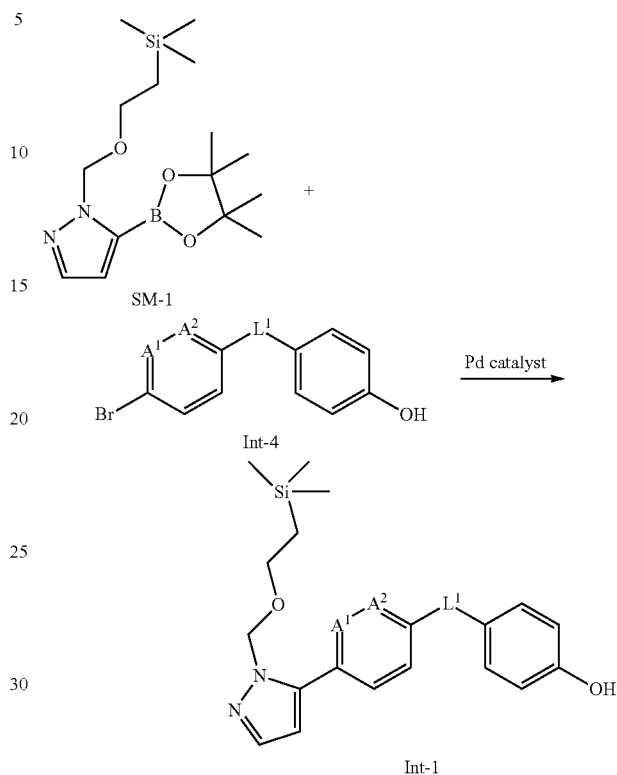

As depicted in Scheme 2, compound Int-4 is allowed to react with 5-(4,4,5,5-tetramethyl-[1,3,2]dioxaborolan-2-yl)-1-(2-trimethylsilanyl-ethoxymethyl)-1H-pyrazole (SM-1) in a suitable solvent (e.g., an aqueous/etheral solvent such as DME/water) and in the presence of a transition metal catalyst (e.g., tetrakis(triphenylphosphine)palladium) to provide the compound Int-1. Alternatively, the compound Int-1 can also be prepared according to the method depicted in Scheme 1 where 1-(2-trimethylsilanyl-ethoxymethyl)-1H-pyrazole-5-boronic acid (SM-2, not shown) is used instead of compound SM-1. Compound SM-1 and SM-2 can be prepared by known methods. Compounds of formula Int-4 are commercially available or can be made by known methods of methods described in the Examples Section below.

A method of making compounds of formula (I) where $A^3$ is N is depicted in Scheme 3 below.

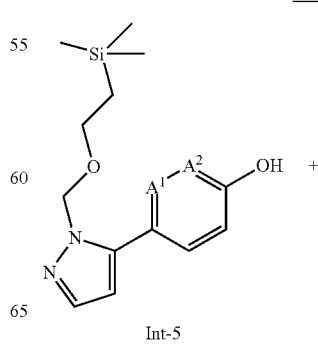

As depicted in Scheme 1, compound Int-1 is allowed to react with compound Int-2 in etheral solvent (e.g., THF) and in the presence of a triarylphosphine (e.g., triphenylphospine or resin-supported triphenylphosphine) to provide Int-3. Int-3 is then hydrolyzed to provide the compound of formula (I).

Compound Int-1 can be prepared according to the method depicted in Scheme 2.

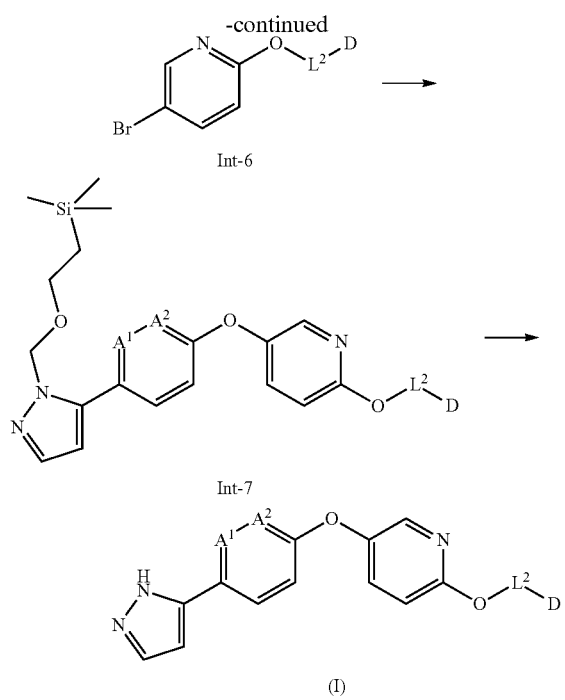

Int-6

Int-7

(I)

As depicted in Scheme 3, compound Int-5 is allowed to react with compound Int-6 in the presence of a transition metal catalyst (e.g., copper iodide) to provide compound Int-7 which is hydrolyzed to provide the compound of formula (I).

Compounds of formula Int-5 can be made by the method described in Scheme 4.

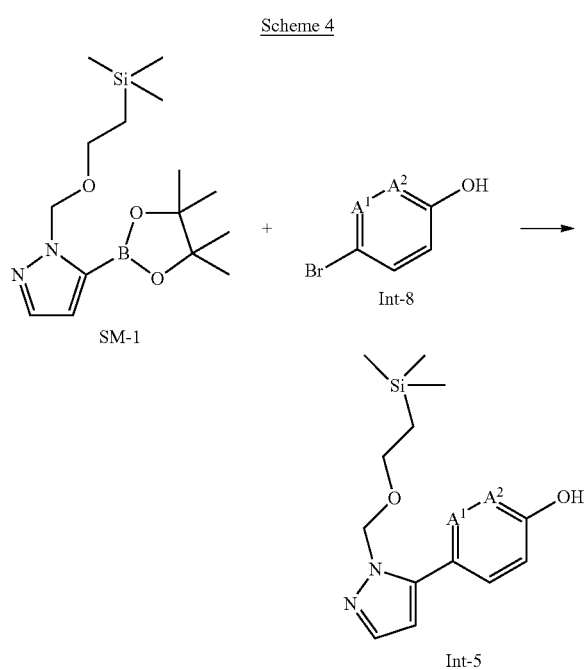

Scheme 4

SM-1

Int-8

Int-5

As depicted in Scheme 4, SM-1 is allowed to react with a compound of formula Int-8 in a suitable solvent (e.g., an aqueous/etheral solvent such as DME/water) and in the presence of a transition metal catalyst (e.g., tetrakis(triphenylphosphine)palladium) to provide the compound of formula Int-5. Compounds of formula Int-8 are commercially available or can be made by known methods.

Compounds of formula Int-6 can be made by the method depicted in Scheme 5 below.

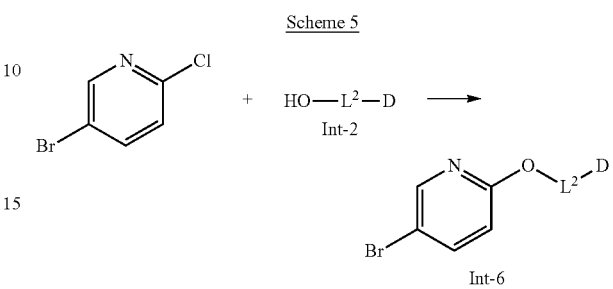

Scheme 5

Int-2

Int-6

As depicted in Scheme 5,5-bromo-2-chloropyridine and the compound Int-2 are allowed to react in the presence of base (e.g., sodium tert-butoxide) to provide the compound for formula Int-6.

The examples which follow are illustrative and particular reagents or conditions could be modified as needed for individual compounds without undue experimentation as recognized by one skilled in the art. Starting materials and reagents are either commercially available or may be prepared by one skilled in the art using methods described in the chemical literature and in the Synthetic Examples section below.

SYNTHETIC EXAMPLES

General Methods

Unless noted otherwise, all reactions are run at room temperature (about 25° C.), under inert atmosphere (e.g., Argon, $N_2$), and under anhydrous conditions. All compounds are characterized by at least one of the following methods: $^1$H NMR, HPLC, HPLC-MS, and/or melting point.

Typically, reaction progress is monitored by thin layer chromatography (TLC) or HPLC-MS. Intermediates and products are purified using at least one of the following methods:
Flash chromatography on silica gel,
Recrystallization,
Chiral HPLC using a 20×500 mm Chiralpak AD-H column, or 20×500 mm Chiralpak OD-H column, and eluting with an isocratic mixture of isopropanol in heptanes with 0.1% diethylamine (DEA) at 7.5 mL/min,
20×250 mm Chiralcel OD-H column, and eluting with an isocratic mixture of isopropanol in heptanes at 7.5 mL/min,
Super Critical Fluid (SCF) Chiral HPLC using a 3.0×25.0 cm RegisPack column, eluting with an isocratic mixture of MeOH, isopropylamine (IPA), and super critical carbon dioxide at 125 bar; 80 mL/min, and/or
Reversed phase HPLC using a C18 semi-preparative column eluting with a gradient of MeCN+0.1% TFA/$H_2O$+0.1% TFA, or MeCN+0.1% formic acid/$H_2O$+0.1% formic acid.

The reported MS data is for observed [M+H]$^+$. For bromine containing compounds, the [M+H]$^+$ is either reported for one or both of the bromine isotopes (i.e., $^{79}$Br and $^{81}$Br).

LC/MS methods used to characterize the compounds of the invention are described in Tables 2a and 2b below.

TABLE 2a

LC/MS Methods and retention times (RT).

| HPLC Method | Time (min) | Mobile Phase | | Flow (mL/min) | Column |
|---|---|---|---|---|---|
| | | H$_2$O (0.1% FA) | CH$_3$CN (0.1% FA) | | |
| 1 | 0 | 95 | 5 | 2.5 | Agilent Zorbax C18 SB 3.5 um |
| | 1.7 | 5 | 95 | 2.5 | 4.6 × 30 mm cartridge |
| | 2 | 5 | 95 | 2.5 | |
| | 2.1 | 95 | 5 | 2.5 | |
| | 2.3 | 95 | 5 | 2.5 | |
| 2 | 0 | 95 | 5 | 1.5 | Agilent Zorbax Eclipse XDB-C8 5 um |
| | 7 | 5 | 95 | 1.5 | 4.6 × 150 mm |
| | 9 | 5 | 95 | 1.5 | |
| | 9.3 | 95 | 5 | 1.5 | |
| | 10 | 95 | 5 | 1.5 | |
| 3 | 0 | 90 | 10 | 0.5 | Thermo Scientific, Aquasil C18, 50 × |
| | 0.5 | 90 | 10 | 0.5 | 2.1 mm column. |
| | 1.5 | 1 | 99 | 0.5 | |
| | 2.5 | 1 | 99 | 0.5 | |
| | 3.0 | 90 | 10 | 0.5 | |
| | 4.0 | 90 | 10 | 0.5 | |

| HPLC Method | Time (min) | Mobile Phase | | Flow (mL/min) | Column |
|---|---|---|---|---|---|
| | | 95% H$_2$O + 5% CH$_3$CN (0.05% Formic Acid) | CH$_3$CN (0.05% Formic Acid) | | |
| 4 | 0 | 90 | 10 | 0.8 | BEH 2.1 × 50 mm C18, 1.7 um |
| | 1.19 | 5 | 95 | 0.8 | particle diameter |
| | 1.7 | 5 | 95 | 0.8 | |
| 5 | 0 | 95 | 5 | 0.6 | Waters HSS T3 2.1 × 100 mm |
| | 4.45 | 0 | 100 | 0.6 | 18 um column |
| | 5 | 0 | 100 | 0.6 | |

List of Abbreviations:
DCE = dichloroethane
DCM = dichloromethane
DME = dimethoxyethane
DMF = dimethylformamide
DMSO = dimethylsulfoxide
EtOAc = ethyl acetate
EtOH = ethanol
IPA = isopropyl alcohol
MeCN = acetonitrile
MeOH = methanol
TEA = triethylamine
TFA = trifluoroacetic acid
THF = tetrahydrofuran

Synthesis of Intermediates

Preparation of 4-{4-[2-(2-Trimethylsilanyl-ethoxymethyl)-2H-pyrazol-3-yl]-phenoxy}-phenol (A)

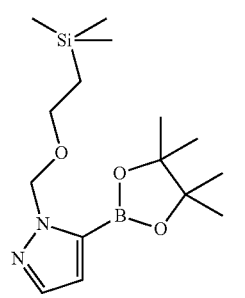

SM-1

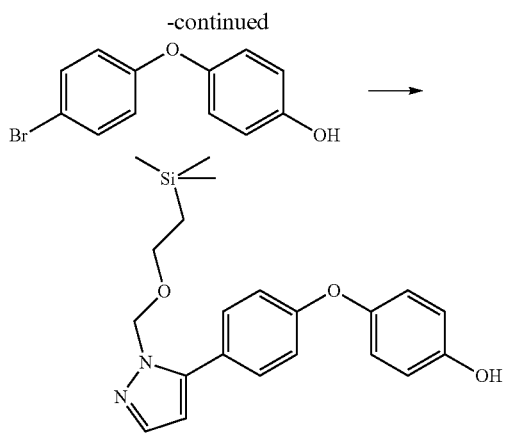

A

A suspension of 4-(4-Bromo-phenoxy)-phenol (7.0 g, 26 mmol), and 5-(4,4,5,5-Tetramethyl-[1,3,2]dioxaborolan-2- yl)-1-(2-trimethylsilanyl-ethoxymethyl)-1H-pyrazole (9.4 g, 39 mmol) in a mixture of DME (120 mL) and 2N aqueous Na$_2$CO$_3$ (33 mL) is sparged with Argon for 30 minutes. Tetrakis(triphenylphosphine)palladium(0) (1.5 g, 1.3 mmol) is added to the mixture, and the mixture is heated to 100° C. After 16 hours, the mixture is cooled to room temperature and poured into water/EtOAc. The organic layer is collected, and the aqueous layer is extracted twice with EtOAc. The combined organic layers are washed with brine, dried over Na$_2$SO$_4$, filtered and concentrated. The residue is purified on SiO2 (EtOAc/heptanes) to provide Intermediate A.

Preparation of 4-{4-[2-(2-Trimethylsilanyl-ethoxymethyl)-2H-pyrazol-3-yl]-benzyl}-phenol (B)

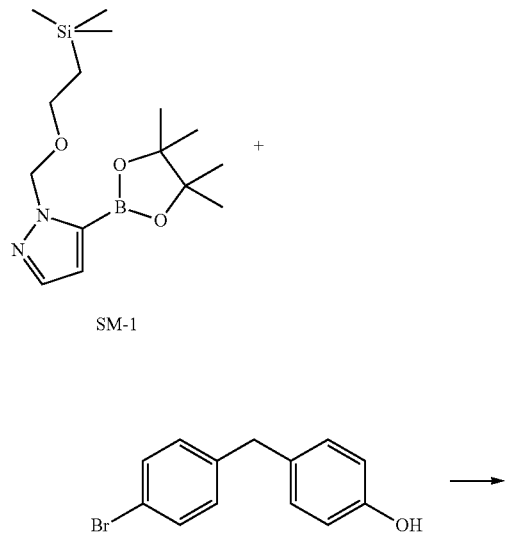

A suspension of 4-(4-Bromo-benzyl)-phenol (2.0 g, 7.6 mmol), compound SM-1 (2.9 g, 9.1 mmol) and tetrakis(triphenylphosphine)palladium(0) (880 mg, 0.76 mmol) in a mixture of DME (20 mL) and 2N aqueous Na$_2$CO$_3$ (9.5 mL) is heated to 130° C. for 1 hour. The mixture is cooled to room temperature, diluted with water, and extracted with ethyl acetate. The organic layer is washed with brine, dried over MgSO$_4$, filtered, and concentrated. The resulting residue is purified on SiO$_2$ (methanol/dichloromethane) to provide Intermediate B.

Preparation of (3E,5E)-6-[2-(2-Trimethylsilanyl-ethoxymethyl)-2H-pyrazol-3-yl]-hepta-1,3,5-trien-3-ol (C)

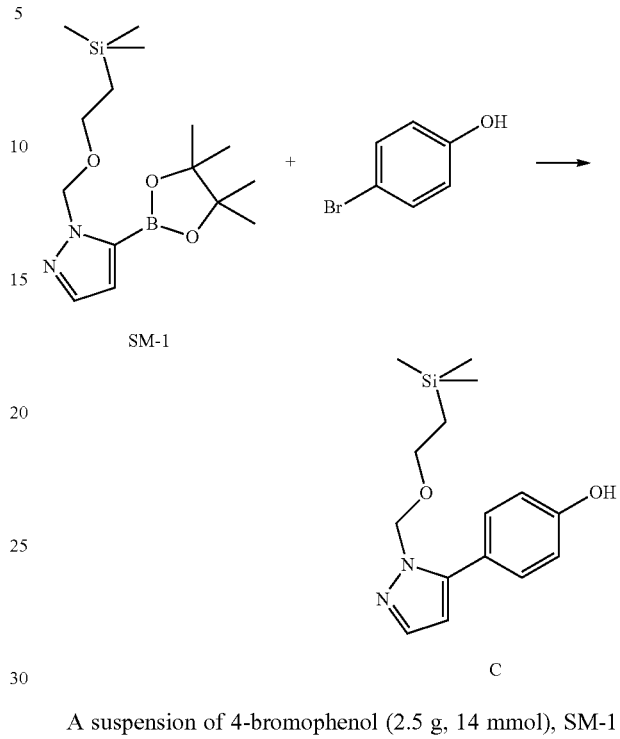

A suspension of 4-bromophenol (2.5 g, 14 mmol), SM-1 (5.6 g, 17 mmol) and tetrakis(triphenylphosphine)palladium (0) (1.6 g, 1.4 mmol) in a mixture of DME (75 mL) and 2N aqueous Na$_2$CO$_3$ (22 mL) is evacuated, and purged thrice with argon, and heated to 100° C. for 16 hours. The reaction is cooled to room temperature, diluted with EtOAc, and washed with water followed by brine. The organic fraction is collected, dried over Na$_2$SO$_4$, filtered, and concentrated. The resulting residue is purified on SiO$_2$ (EtOAc/heptane) to provide Intermediate C.

Preparation of 2-(4-benzyloxy-phenoxy)-5-bromo-pyridine (D)

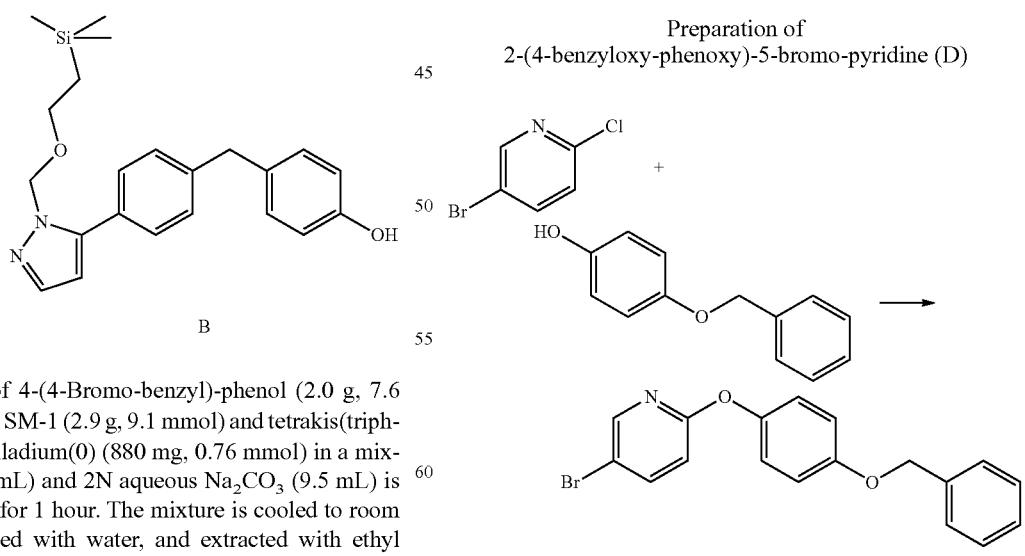

Potassium tert-butoxide (7 g, 62 mmol) is added to a solution of 5-bromo-2-chloro-pyridine (10 g, 52 mmol) and 4-benzyloxy-phenol (10.4 g, 52 mmol) in DMF (104 mL). The mixture is heated to 110° C. for 3.5 hours then cooled. The solution is then poured into water/ethyl acetate, and the organic layer is collected. The aqueous layer is extracted twice with EtOAc, and the combined organic layers are washed with brine. The organic layer is then dried over Na$_2$SO$_4$, filtered and concentrated. The resulting residue is purified on SiO$_2$ (EtOAc/heptanes) to provide Intermediate D.

Preparation of 4-(5-Bromo-pyridin-2-yloxy)-phenol (E)

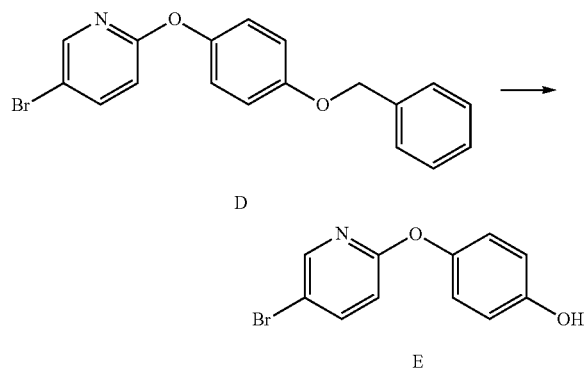

A mixture of Intermediate D (9.5 g, 27 mmol), pentamethyl benzene (8 g, 54 mmol), and trifluoroacetic acid (57 mL, 750 mmol) is stirred at room temperature for 2.5 hours. The mixture is concentrated and the resulting residue is dissolved in EtOAc. The organic layer is washed with saturated sodium bicarbonate followed by brine, dried over Na$_2$SO$_4$, filtered and concentrated. The resulting residue is purified on SiO$_2$ (EtOAc/heptanes) to provide Intermediate D.

Preparation of 4-{5-[2-(2-trimethylsilanyl-ethoxymethyl)-2H-pyrazol-3-yl]-pyridin-2-yloxy}-phenol (F)

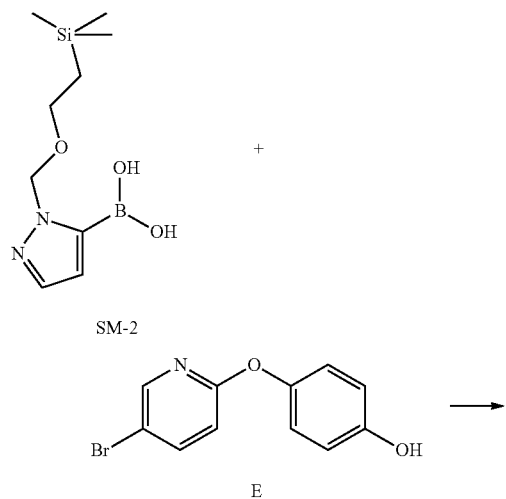

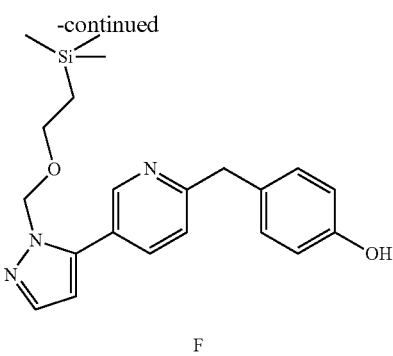

A suspension of Intermediate E (6.0 g, 23 mmol) and 1-(2-trimethylsilanyl-ethoxymethyl)-1H-pyrazole-5-boronic acid (SM-2) (6.6 g, 27 mmol) in a mixture of DME (60 mL) and 2N aqueous Na$_2$CO$_3$ (33 mL) is sparged with Argon for 30 minutes. The mixture is treated with tetrakis(triphenylphosphine)palladium(0) (2.6 g, 2 mmol) and heated to 100° C. for 16 hours. The solution is cooled, poured into water/EtOAc, and the organic layer is collected. The aqueous layer is extracted twice with EtOAc, and the combined organic layers are washed with brine, dried over Na$_2$SO$_4$, filtered and concentrated. The residue is purified on SiO$_2$ (EtOAc/heptanes) to provide F.

Synthesis of Compounds of Formula I

General Method A Through E (Protocols for Mitsunobu Coupling)

Example of General Method A

Preparation of 3-{4-[4-(1H-Pyrazol-3-yl)-phenoxy]-phenoxymethyl}-pyridine (Example 34)

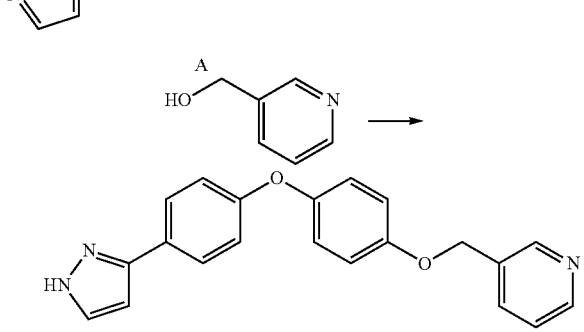

PS—PPh$_3$ resin (97 mg, 0.3 mmol) is added to a solution of pyridin-3-yl-methanol (21 mg, 0.2 mmol) and Intermediate A (40 mg, 0.1 mmol) in THF (1 mL). Di-tert-butyl azodicarboxylate (34 mg, 0.15 mmol) and THF (0.5 mL) are then added, and the mixture is shaken at room temperature. After 16 hours, additional di-tert-butyl azodicarboxylate (34 mg, 0.15 mmol) and THF (0.5 mL) are added and the reaction is stirred for 16 hours. The mixture is filtered, and the resin is washed with THF, DCE, THF, DCE, and THF (0.5 mL each). The combined filtrates are concentrated, and the resulting residue is dissolved in DCE (1 mL) and 10% citric acid (0.5 mL). The layers are separated using phase separating cartridges, and the product extracted 3 times with 0.5 mL of DCE, and evaporated in vacuo to provide the crude product. The material is dissolved in DCE (1 mL), treated with 4N HCl (125 µL), and shaken. After 16 hours, the mixture is concentrated, and the crude is purified by reversed phase HPLC to provide 34.

Example of General Method B

5-[4-[4-(1-Methyl-1H-imidazol-2-ylmethoxy)-phenoxy]-phenyl]-1H-pyrazole (Example 26)

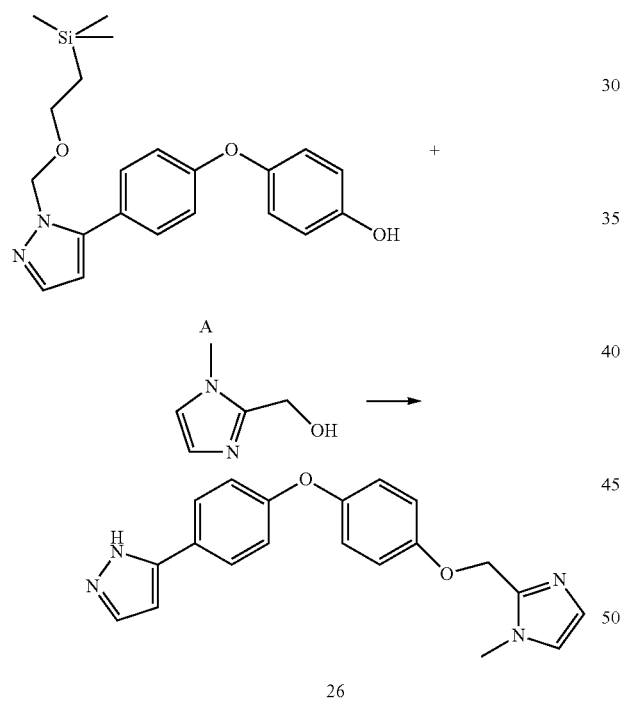

A solution of Intermediate A (124 mg, 0.32 mmol), (1-methyl-1H-imidazol-2-yl)-methanol (55 mg, 0.48 mmol), and triphenylphosphine (140 mg, 0.52 mmol) in THF (1.5 mL) is purged with nitrogen and treated with diisopropyldiazodiacarboxylate (75 uL, 0.52 mmol). The mixture is stirred for 16 hours. Additional triphenylphosphine (140 mg, 0.52 mmol) and diisopropyldiazodiacarboxylate (75 uL, 0.52 mmol) are added and stirring is continued. After 48 hours, 4N HCl (2 mL) is added and the solution stirred overnight. The mixture is concentrated, and the residue is purified on reversed phase HPLC to provide 26.

Example of General Method C

Preparation of (±) 3-{4-[5-(2H-Pyrazol-3-yl)-pyridin-2-yloxy]-phenoxymethyl}-morpholine (Example 16)

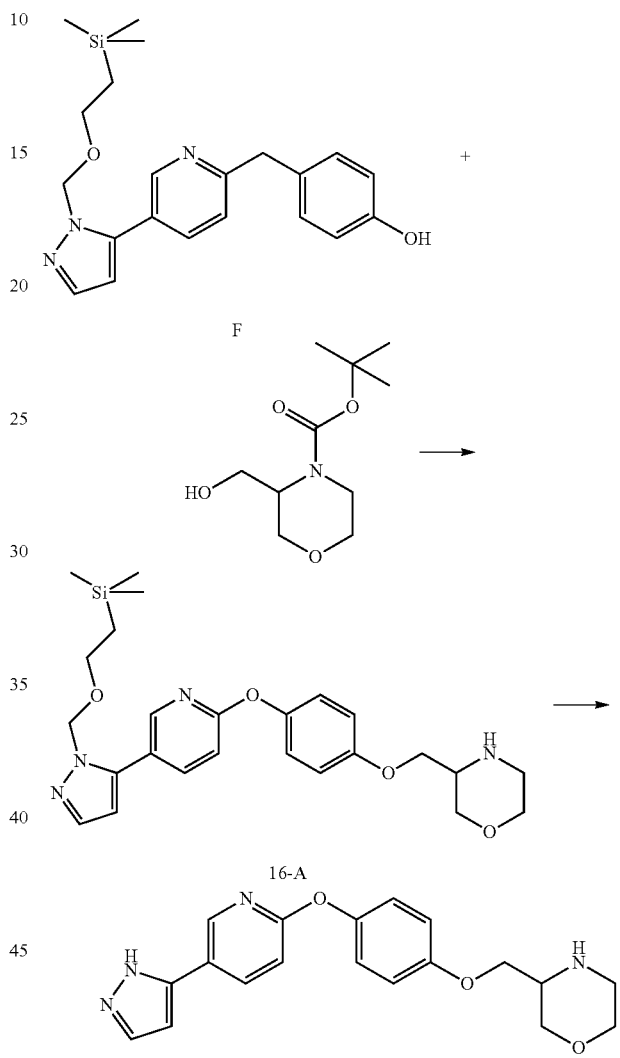

PS—PPh₃ resin (175 mg, 0.52 mmol) is added to a solution of Intermediate F (100 mg, 0.26 mmol), and 3-hydroxymethyl-morpholine-4-carboxylic acid tert-butyl ester (102 mg, 0.47 mmol) in THF (3 mL). The mixture is stirred for 10 minutes, treated with di tert-butydiazodicarboxylate (120 mg, 0.52 mmol), and heated to 60° C. After 16 hours, the mixture is treated with water, and the product extracted with EtOAc. The organic layer is concentrated, and the resulting residue is purified on SiO₂ (heptanes/EtOAc) to provide 16-A. Intermediate 16-A is taken up in 4N HCl in dioxane (1 mL) and heated to 45° C. After 15 minutes, the mixture is treated with diisopropylamine (1 mL) and concentrated. The resulting residue is purified on SiO₂ (DCM/MeOH/NH₄OH) to provide 16.

Example of General Method D

Preparation of (R)-5-{4-[4-(2H-Pyrazol-3-yl)-benzyl]-phenoxy}-piperidin-2-one (Example 18)

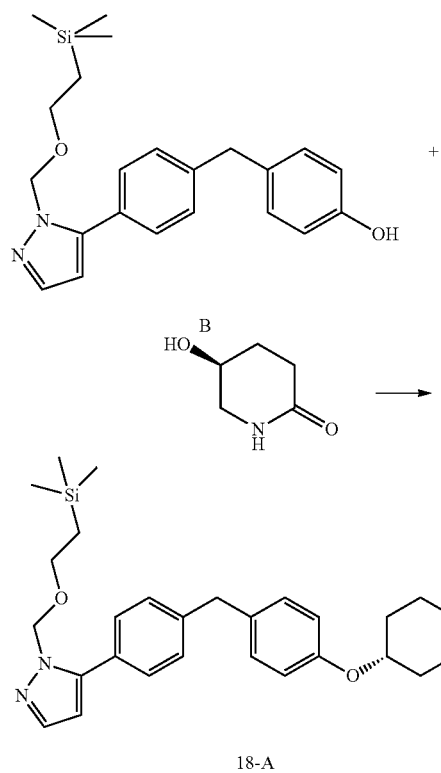

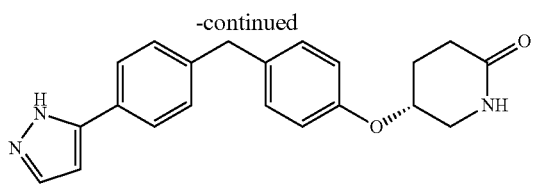

18

PS—PPh$_3$ resin (810 mg, 0.52 mmol) and di tert-butydiazodicarboxylate (372 mg, 1.6 mmol) are added to solution of Intermediate B (307 mg, 0.81 mmol) and (S)-5-Hydroxypiperidin-2-one (190 mg, 1.6 mmol) in THF (8 mL). The mixture is stirred for 16 hours, filtered, diluted with EtOAc, and washed with water. The organic layer is collected and concentrated. The resulting residue is purified on SiO$_2$ (heptanes/EtOAc) to provide 18-A. Intermediate 18-A is taken up in 4N HCl in dioxane (3 mL) and heated to 45° C. After 1 hour, the mixture is partitioned between EtOAc and saturated NaHCO$_3$. The organic layer is collected, dried over Na$_2$SO$_4$, filtered, and concentrated. The resulting residue is purified on SiO$_2$ (DCM/MeOH) to provide 18.

Table 3 provides a summary of the key reagents used to prepare Examples 1-95 according to general methods A, B, C, D, E, or F.

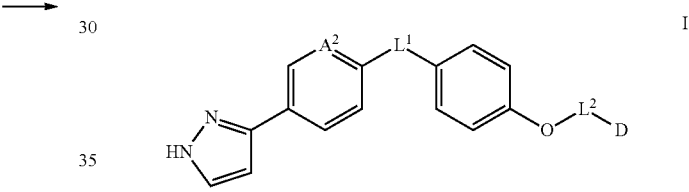

I

TABLE 3

Examples synthesized by General Method A, B, C, D, E, or F

| Ex # | A$^2$ | L$^1$ | —L$^2$—D | Synthesis Method | MS Method | Rt (min) | [M + H]$^+$ |
|---|---|---|---|---|---|---|---|
| 1 | C | O | | A | 4 | 0.78 | 350.0 |
| 2 | C | O | | A | 4 | 0.77 | 350.2 |
| 3 | N | O | | C | 3 | 2.95 | 345.3 |
| 4 | C | O | | A | 4 | 0.88 | 323 |

TABLE 3-continued
Examples synthesized by General Method A, B, C, D, E, or F
| Ex # | A² | L¹ | —L²—D | Synthesis Method | MS Method | Rt (min) | [M + H]⁺ |
|---|---|---|---|---|---|---|---|
| 5 | C | O | 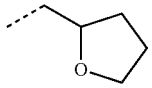 | A | 4 | 0.95 | 336.8 |
| 7 | C | O | 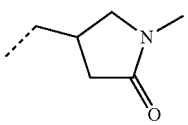 | A | 4 | 0.79 | 364.2 |
| 8 | C | O | 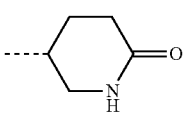 | A | 4 | 0.71 | 350.9 |
| 9 | C | O | 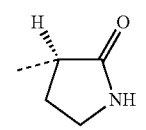 | A | 4 | 0.71 | 336.1 |
| 10 | C | O | 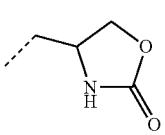 | A | 4 | 0.73 | 352 |
| 11 | C | O | 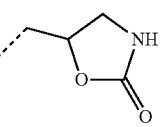 | A | 4 | 0.71 | 352.1 |
| 12 | C | O | 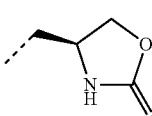 | B | 1 | 1.37 | 352.2 |
| 13 | C | O | 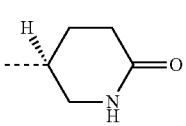 | B | 2 | 4.94 | 350.1 |
| 14 | C | O | 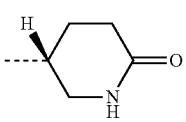 | B | 2 | 4.95 | 350.2 |
| 15 | C | O | 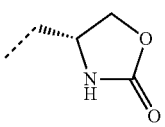 | B | 1 | 1.37 | 352.2 |
| 16 | N | O | 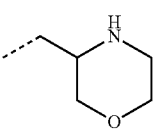 | C | 2 | 3.56 | 353.2 |
| 17 | N | O | 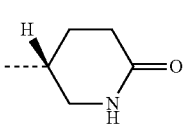 | C | 2 | 0.61 | 353.2 |

TABLE 3-continued

Examples synthesized by General Method A, B, C, D, E, or F

| Ex # | A² | L¹ | —L²—D | Synthesis Method | MS Method | Rt (min) | [M + H]⁺ |
|---|---|---|---|---|---|---|---|
| 18 | C | C | (4-piperidinone, stereochemistry shown) | D | 4 | 0.73 | 348.2 |
| 20 | C | C | (4-ethyl-oxazolidin-2-one) | D | 3 | 2.77 | 350.3 |
| 21 | C | O | (propyl-pyrrolidinone) | A | 4 | 0.83 | 364.5 |
| 22 | C | O | (ethyl-morpholine) | A | 4 | 0.51 | 366.2 |
| 23 | C | O | (butyl-pyrrolidinone) | A | 4 | 0.82 | 378.4 |
| 24 | N | O | (4-ethyl-oxazolidin-2-one) | C | 1 | 1.26 | 353.27 |
| 25 | C | C | (ethyl-morpholine) | D | 3 | 2.6 | 364.4 |
| 26 | C | O | (N-methylimidazole-ethyl) | B | 2 | 0.72 | 347.1 |
| 27 | C | O | (imidazole-ethyl) | B | 2 | 0.61 | 333.5 |
| 28 | C | O | (benzimidazole-ethyl) | B | 2 | 1.1 | 383.6 |
| 29 | C | O | (pyridine-ethyl) | A | 4 | 0.69 | 358.2 |
| 30 | C | O | (furan-methyl) | A | 4 | 1.03 | 333.1 |

TABLE 3-continued

Examples synthesized by General Method A, B, C, D, E, or F

| Ex # | A² | L¹ | —L²—D | Synthesis Method | MS Method | Rt (min) | [M + H]⁺ |
|---|---|---|---|---|---|---|---|
| 31 | C | O | benzyl with methyl branch | A | 4 | 1.24 | 371.1 |
| 32 | C | O | 1-phenylethyl | A | 4 | 1.25 | 371.3 |
| 33 | C | O | (pyridin-2-yl)methyl | A | 4 | 0.72 | 358.2 |
| 34 | C | O | (pyridin-3-yl)methyl | A | 4 | 0.76 | 344.2 |
| 35 | C | O | (pyridin-4-yl)methyl | A | 4 | 0.7 | 344.1 |
| 36 | C | O | imidazo[2,1-b]thiazol-6-ylmethyl | A | 4 | 0.81 | 389.1 |
| 37 | C | O | (4-(methylsulfonyl)phenyl)methyl | A | 4 | 0.94 | 421.2 |
| 38 | C | O | thiazol-4-ylmethyl | A | 4 | 0.94 | 350.1 |
| 39 | C | O | (1H-pyrrolo[2,3-b]pyridin-5-yl)methyl | A | 4 | 0.92 | 383.2 |
| 40 | C | O | (pyridin-4-yl)methyl | A | 4 | 0.68 | 358.2 |
| 41 | C | O | (1H-benzimidazol-2-ylamino)ethyl | A | 4 | 0.68 | 412.2 |
| 42 | C | O | (2-methyl-1H-imidazol-1-yl)ethyl | A | 4 | 0.62 | 361.2 |

TABLE 3-continued
Examples synthesized by General Method A, B, C, D, E, or F
| Ex # | A² | L¹ | —L²—D | Synthesis Method | MS Method | Rt (min) | [M + H]⁺ |
|---|---|---|---|---|---|---|---|
| 43 | C | O | 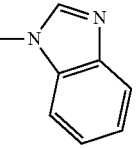 | A | 4 | 0.73 | 397.2 |
| 44 | C | O | 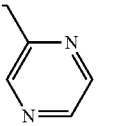 | A | 4 | 0.89 | 345.2 |
| 45 | C | O | 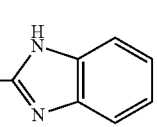 | A | 4 | 0.68 | 397.2 |
| 46 | C | O | 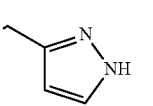 | A | 3 | 2.9 | 333.3 |
| 47 | C | O | 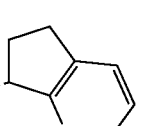 | A | 4 | 0.9 | 370.2 |
| 48 | C | O | 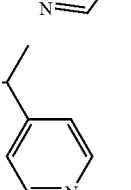 | A | 4 | 0.7 | 358.2 |
| 49 | C | O | 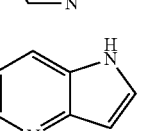 | A | 4 | 0.58 | 383.2 |
| 50 | C | O | 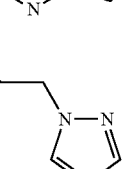 | A | 4 | 0.91 | 361.2 |
| 51 | C | O | 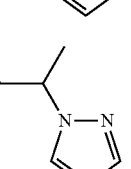 | A | 4 | 0.96 | 375.2 |
| 52 | C | O | 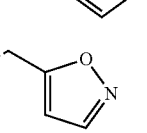 | A | 4 | 0.89 | 334.2 |
| 53 | C | O | 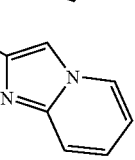 | A | 4 | 0.59 | 383.2 |

TABLE 3-continued

Examples synthesized by General Method A, B, C, D, E, or F

| Ex # | A² | L¹ | —L²—D | Synthesis Method | MS Method | Rt (min) | [M + H]⁺ |
|---|---|---|---|---|---|---|---|
| 54 | C | O | oxazol-4-ylmethyl | A | 4 | 0.84 | 334.2 |
| 55 | C | O | 2-(1H-pyrazol-4-yl)ethyl | A | 4 | 0.82 | 347.2 |
| 56 | C | O | (1-methyl-1H-1,2,4-triazol-5-yl)methyl | A | 4 | 0.75 | 348.2 |
| 57 | C | O | (5-(furan-2-yl)-1-methyl-1H-pyrazol-3-yl)methyl | A | 4 | 1.02 | 413.3 |
| 58 | C | O | (R)-1-(pyridin-2-yl)ethyl | A | 4 | 0.9 | 358.2 |
| 59 | C | O | (S)-1-(pyridin-2-yl)ethyl | A | 4 | 0.9 | 358.2 |
| 60 | C | O | (2-methyloxazol-4-yl)methyl | A | 4 | 0.88 | 348.2 |
| 61 | C | O | (1-methyl-1H-pyrazol-5-yl)methyl | A | 4 | 0.86 | 347.2 |
| 62 | C | O | benzyl | A | 4 | 1.12 | 343.2 |
| 63 | C | O | furan-3-ylmethyl | A | 4 | 1.01 | 333.1 |
| 64 | C | O | benzo[d]thiazol-2-ylmethyl | A | 4 | 1.1 | 400.1 |

TABLE 3-continued

Examples synthesized by General Method A, B, C, D, E, or F

| Ex # | A² | L¹ | —L²—D | Synthesis Method | MS Method | Rt (min) | [M + H]⁺ |
|---|---|---|---|---|---|---|---|
| 65 | C | O | 3-methyl-1H-pyrazol-1-yl | A | 4 | 0.85 | 347 |
| 66 | C | O | 1H-pyrazol-3-yl | A | 4 | 1.16 | 356.9 |
| 67 | C | O | 4-methylthiazol-5-yl | A | 4 | 0.93 | 378.1 |
| 68 | C | O | thiophen-2-yl | A | 4 | 1.13 | 363.2 |
| 69 | C | O | thiophen-3-yl | A | 4 | 1.08 | 349.1 |
| 70 | C | O | thiazol-5-yl | A | 4 | 0.87 | 350.3 |
| 71 | C | O | benzothiazol-5-yl | A | 4 | 1.01 | 400.1 |
| 72 | C | O | isoxazol-4-yl | A | 4 | 0.92 | 348.2 |
| 73 | C | O | thiazol-2-yl | A | 4 | 0.92 | 350.9 |
| 74 | C | O | 4-methyloxazol-5-yl | A | 4 | 0.87 | 348.9 |
| 75 | C | O | pyrimidin-2-yl | A | 4 | 0.77 | 345.1 |
| 76 | C | O | imidazo[1,2-a]pyridin-6-yl | A | 4 | 0.58 | 383.1 |
| 77 | C | O | 4-methyl-1,2,3-thiadiazol-5-yl | A | 4 | 0.94 | 366.1 |

TABLE 3-continued

Examples synthesized by General Method A, B, C, D, E, or F

| Ex # | A² | L¹ | —L²—D | Synthesis Method | MS Method | Rt (min) | [M + H]⁺ |
|---|---|---|---|---|---|---|---|
| 78 | C | O | oxazole | A | 4 | 0.83 | 333.9 |
| 79 | C | O | isobutyl-pyrazole | A | 4 | 0.98 | 375.1 |
| 80 | C | O | pyridinyl-pyrazole | A | 4 | 1.05 | 410.2 |
| 81 | C | O | benzimidazole | A | 3 | 2.7 | 383.4 |
| 82 | C | O | ethyl-tetrahydropyran | A | 4 | 1.03 | 365.9 |
| 83 | C | O | tetrahydropyran | A | 4 | 1.01 | 351.9 |
| 84 | C | O | tetrahydropyran | A | 4 | 0.98 | 351.4 |
| 85 | C | O | γ-butyrolactone | A | 4 | 0.82 | 351.1 |
| 86 | C | O | γ-butyrolactone | A | 3 | 2.76 | 351.3 |
| 87 | C | O | γ-butyrolactone | A | 4 | 0.82 | 337.1 |
| 88 | C | O | γ-butyrolactone | A | 4 | 0.82 | 337.1 |
| 89 | C | O | tetrahydropyran | A | 4 | 0.92 | 337.5 |

TABLE 3-continued

Examples synthesized by General Method A, B, C, D, E, or F

| Ex # | A² | L¹ | —L²—D | Synthesis Method | MS Method | Rt (min) | [M + H]⁺ |
|------|----|----|-------|------------------|-----------|----------|----------|
| 90 | C | O | ![structure] | A | 4 | 0.88 | 323.2 |
| 91 | C | O | ![structure] | A | 4 | 1.03 | 351.1 |
| 92 | C | O | ![structure] | A | 4 | 0.93 | 337.9 |
| 93 | C | O | ![structure] | A | 4 | 1.12 | 366.3 |
| 94 | C | O | ![structure] | A | 4 | 0.95 | 337 |

Example 6

Preparation of (R)-5-{5-[4-(2H-Pyrazol-3-yl)-phenoxy]-pyridin-2-yloxy}-piperidin-2-one (6)

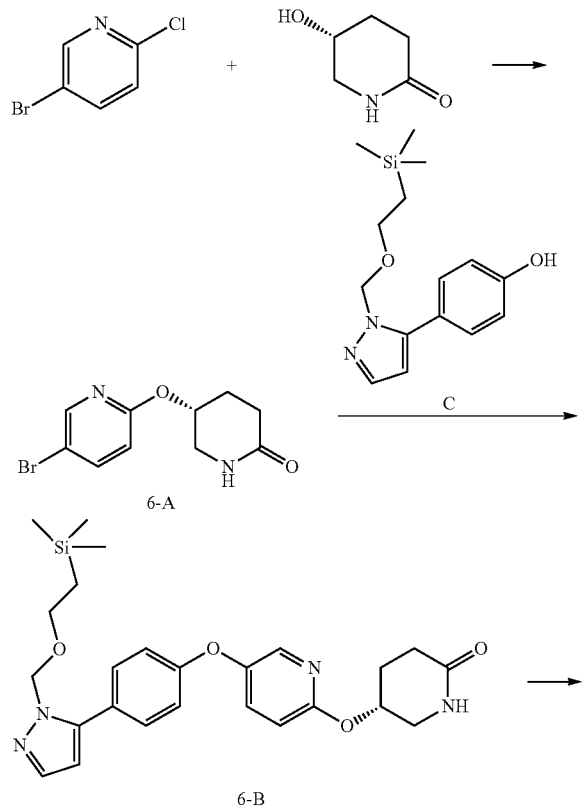

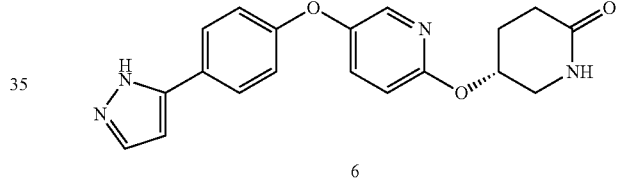

Sodium tert-butoxide (439 mg, 4.6 mmol) is added to a solution of (R)-5-hydroxy-piperidin-2-one (287 mg, 2.5 mmol) in DMF (12 mL) at 0° C., and the mixture is warmed to room temperature. After 30 min, 5-bromo-2-cholo-pyridine (400 mg, 2.1 mmol) is added, and the mixture is heated to 100° C. for 30 min. Upon cooling, the solution is poured into water/EtOAc, and phases are separated. The aqueous layer is extracted twice with EtOAc. The combined organic layers are washed with brine, dried over Na₂SO₄, filtered and concentrated. The residue is purified on reversed phase HPLC to provide Intermediate 6-A. A suspension of Intermediate C (278 mg, 0.96 mmol), Intermediate 6-A (315 mg, 1.20 mmol), potassium phosphate (763 mg, 3.60 mmol), and 2-picolinic acid (30 mg, 0.24 mmol) in DMSO (10 mL) is sparged with Argon for 10 minutes. Copper iodide (23 mg, 0.12 mmol) is added and the mixture is heated to 120° C. for 2 hours in a microwave reactor. Upon cooling, the solution is diluted with EtOAc (10 mL) and filtered through a pad of Diatomaceous earth. The filtrate is washed with water and brine, dried over Na₂SO₄, filtered and concentrated. The resulting residue is purified by reverse phase HPLC to provide the Intermediate 6-B. 4N HCl in dioxane (2 mL) is added to a solution of Intermediate 6-B (120 mg, 0.25 mmol) in 1,4-dioxane (1 mL), and the resulting solution is stirred at 45° C. for 30 min. during which time a precipitate forms. The solids are isolated by filtration, and purified by reverse phase HPLC to provide an oil. The oil is then dissolved in MeOH (2 mL), and passed through PL-HCO$_3$ MP-resin. The resin is washed with MeOH (2 mL), and the combined extracts are concentrated to provide 6. LC/MS Method 3: Rt=2.79 min; ES+ m/z [M+H]$^+$=351.3.

Example 7

Preparation of (S)-5-{5-[4-(2H-Pyrazol-3-yl)-phenoxy]-pyridin-2-yloxy}-piperidin-2-one (7)

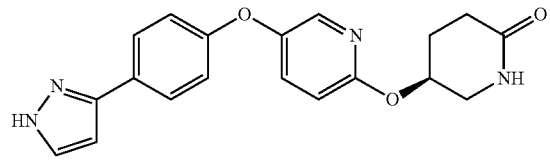 [SMILES: O=C1CC[C@H](Oc2ccc(Oc3ccc(-c4cc[nH]n4)cc3)cn2)CN1]

Compound 7 is prepared according to the procedure described above for the synthesis of Compound 6. LC/MS Method 3: Rt=2.79 min; ES+ m/z [M+H]+=351.3.

Example 95

Preparation of (R)-5-{4-[6-(2H-pyrazol-3-yl)-pyridin-3-yloxy]-phenoxy}-piperidin-2-one (95)

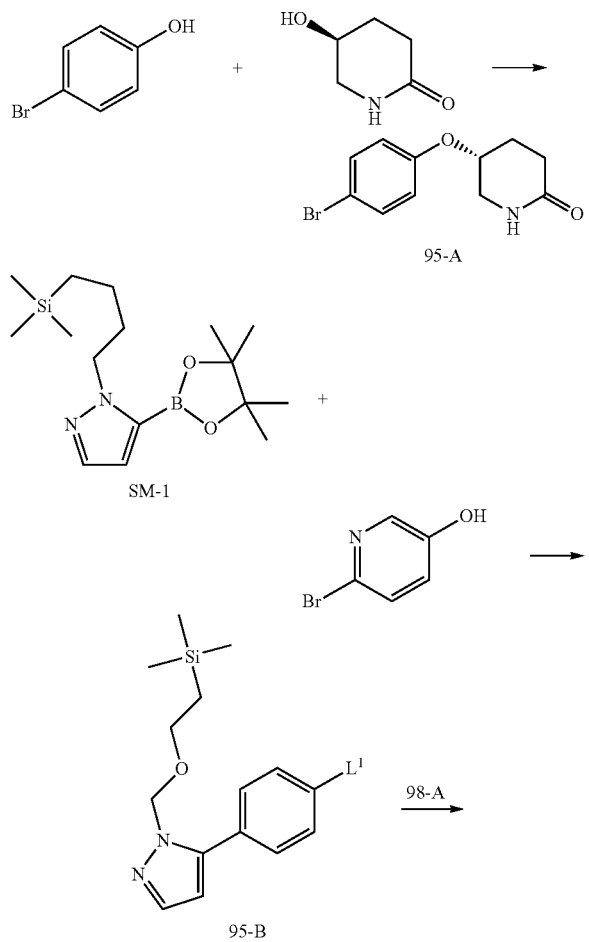

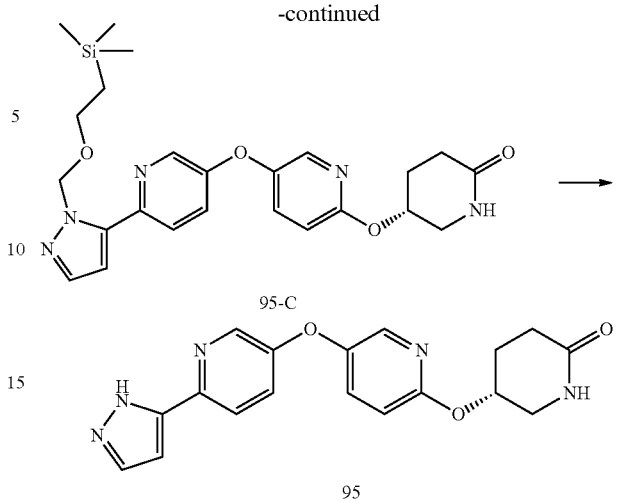

PS—PPh$_3$ resin (3 mmol/g; 1.93 g, 5.8 mmol) is added to a solution of 4-bromophenol (500 mg, 2.9 mmol) and (S)-5-hydroxy-piperidin-2-one (665 mg, 5.8 mmol) in THF (20 mL). The suspension is heated to 65° C. and treated with di-tert-butylazo-dicarboxylate (1.33 g, 5.8 mmol). The resulting mixture is stirred at 65° C. for 16 hours then cooled to room temperature. The mixture is filtered through Diatomaceous earth and washed with THF (30 mL). The filtrate is concentrated, and the resulting residue is purified on SiO$_2$ (EtOAc/heptane, then MeOH/DCM) to provide Intermediate 95-A.

6-Bromo-pyridin-2-ol (200 m g, 1.15 mmol) and tetrakis(triphenylphosphine)palladium(0) (66 mg, 0.06 mmol) are suspended in DME (5 mL). After 10 min, SM-1 (410 mg, 1.26 mmol) and 2N aqueous Na$_2$CO$_3$ (1.7 mL) are added. The reaction is then purged twice with argon and heated to 100° C. for 20 minutes in a microwave reactor. Upon cooling the reaction is diluted with EtOAc, washed with water and brine, dried over Na$_2$SO$_4$, filtered, and concentrated. The resulting residue is purified on SiO$_2$ (EtOAc/heptane) to provide Intermediate 95-B.

A suspension of Intermediate 95-B (200 mg, 0.68 mmol), Intermediate 95-A (370 mg, 1.37 mmol), cesium carbonate (447 mg, 1.37 mmol), and N,N-dimethylglycine hydrochloride (48 mg, 0.34 mmol) in DMSO (5 mL) is sparged with Argon for 10 minutes. Copper iodide (26 mg, 0.14 mmol) is added to and the mixture is heated to 140° C. for 2 hours in a microwave reactor. Upon cooling, the solution is poured into water/EtOAc, and phases are separated. The aqueous layer is then extracted twice with EtOAc. The combined organic layers are washed with brine, dried over Na$_2$SO$_4$, filtered and concentrated. The residue is purified on SiO$_2$ (EtOAc/heptanes, then MeOH/DCM) to provide Intermediate 95-C.

4N HCl in dioxane (1 mL) is added to a solution of Intermediate 95-C (82 mg, 0.17 mmol) in 1,4-dioxane (1 mL). The resulting solution is stirred at 45° C. for 30 minutes during which time a precipitate forms. The resulting solid are filtered and purified on reversed phase HPLC to provide an oil. The oil is then dissolved in MeOH (2 mL) and filtered through PL-HCO$_3$ MP-resin. The resulting resin is washed with MeOH (2 mL) and the combined solvents are concentrated to provide 95. LC/MS Method 3: Rt=2.66 min; ES+ m/z [M+H]$^+$=351.3.

Assessment of Biological Properties

Compounds are assessed for the ability to interact with human LTA$_4$ hydrolase in an enzymatic assay that measures the ability of the enzyme to cleave the peptide bond of arginyl-aminomethylcoumarin (Arg-AMC). LTA4H Enzyme (1 nM final), Arg-AMC substrate (50 μM final), and compound are combined in a reaction buffer (50 mM Tris-HCl (pH 7.5), 100 mM KCl, 0.5% bovine serum albumin) at room temperature for 1 h. The formation of product is assessed by measuring the fluorescence of aminomethylcoumarin product (excitation wavelength 380 nm/emission wavelength 460 nm).

In general, the preferred potency range ($IC_{50}$) of compounds in the above assay is between 0.1 nM to 10,000 nM, the more preferred potency range is 0.1 nM to 100 nM, and the most preferred potency range is 0.1 nM to 10 nM. The potencies of representative compounds of the invention in the enzyme assay are shown in Table 4 below.

TABLE 4

IC50 values of LTA4H Enzyme assay.

| Example | $IC_{50}$ (nM) |
| --- | --- |
| 1 | 0.2 |
| 2 | 0.2 |
| 3 | 0.2 |
| 4 | 3.9 |
| 5 | 6.8 |
| 6 | 3.5 |
| 7 | 0.5 |
| 8 | 0.5 |
| 9 | 76.7 |
| 10 | 0.2 |
| 11 | 1.3 |
| 12 | 0.1 |
| 13 | 0.5 |
| 14 | 0.3 |
| 15 | 0.3 |
| 16 | 0.2 |
| 17 | 1.5 |
| 18 | 0.8 |
| 19 | 1.9 |
| 20 | 0.6 |
| 21 | 0.7 |
| 22 | 0.2 |
| 23 | 0.7 |
| 24 | 0.2 |
| 25 | 0.5 |
| 26 | 1.2 |
| 27 | 2.2 |
| 28 | 1.4 |
| 29 | 4.9 |
| 30 | 65.6 |
| 31 | 900 |
| 32 | 360 |
| 33 | 5.2 |
| 34 | 1.5 |
| 35 | 3.9 |
| 36 | 6 |
| 37 | 3.5 |
| 38 | 3.3 |
| 39 | 7.6 |
| 40 | 3.2 |
| 41 | 0.2 |
| 42 | 0.3 |
| 43 | 1.3 |
| 44 | 1.1 |
| 45 | 1.7 |
| 46 | 6.1 |
| 47 | 82.4 |
| 48 | 16.9 |
| 49 | 1.2 |
| 50 | 1.2 |
| 51 | 4 |
| 52 | 4.1 |
| 53 | 3.7 |
| 54 | 4.2 |
| 55 | 7 |
| 56 | 0.6 |
| 57 | 11 |
| 58 | 44 |
| 59 | 42.7 |
| 60 | 3.9 |
| 61 | 1.4 |
| 62 | 142.3 |
| 63 | 52.9 |
| 64 | 44.2 |
| 65 | 12.9 |
| 66 | 959.2 |
| 67 | 11.2 |
| 68 | 820 |
| 69 | 65.3 |
| 70 | 4.9 |
| 71 | 59.5 |
| 72 | 6.1 |
| 73 | 10.4 |
| 74 | 17.9 |
| 75 | 6.6 |
| 76 | 0.9 |
| 77 | 1 |
| 78 | 2.8 |
| 79 | 2.7 |
| 80 | 1.9 |
| 81 | 14.2 |
| 82 | 7.9 |
| 83 | 2.9 |
| 84 | 4.6 |
| 85 | 0.8 |
| 86 | 0.8 |
| 87 | 23.1 |
| 88 | 16.4 |
| 89 | 4.8 |
| 90 | 2.4 |
| 91 | 10.7 |
| 92 | 3.3 |
| 93 | 26.9 |
| 94 | 14.1 |
| 95 | 1.6 |

Compounds of the invention are additionally tested in a human whole blood assay to determine their ability to inhibit the synthesis of $LTB_4$ in a cellular system. Compounds are combined with heparinized human whole blood and incubated for 15 minutes at 37° C. Calcimycin (20 μM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma $LTB_4$ concentrations are then measured using an antibody-based homogenous time-resolved fluorescence method (CisBio, Bedford, Mass.).

In general, the preferred potency range ($IC_{50}$) of compounds in the above assay is between 10 nM to 10,000 nM, the more preferred potency range is 10 nM to 1000 nM, and the most preferred potency range is 10 nM to 100 nM. The potencies of representative compounds of the invention in the WHB assays are shown in Table 5.

TABLE 5

$IC_{50}$ values of $LTB_4$ production inhibition assay in human whole blood.

| Ex. No. | $IC_{50}$ (nM) |
| --- | --- |
| 1 | 246 |
| 2 | 163 |
| 3 | 142 |

TABLE 5-continued

IC$_{50}$ values of LTB$_4$ production inhibition assay in human whole blood.

| Ex. No. | IC$_{50}$ (nM) |
|---|---|
| 4 | 1037 |
| 5 | 1347 |
| 6 | 1079 |
| 7 | 280 |
| 8 | 222 |
| 9 | 5000 |
| 10 | 126 |
| 11 | 573 |
| 12 | 104 |
| 13 | 214 |
| 14 | 178 |
| 15 | 150 |
| 16 | 52 |
| 17 | 425 |
| 18 | 581 |
| 19 | 554 |
| 20 | 229 |
| 21 | 813 |
| 22 | 179 |
| 23 | 529 |
| 24 | 123 |
| 25 | 123 |
| 26 | 2106 |
| 27 | 1838 |
| 28 | 5000 |
| 29 | 2281 |
| 30 | 5000 |
| 31 | 5000 |
| 32 | 5000 |
| 33 | 3362 |
| 34 | 2537 |
| 35 | 1783 |
| 36 | 4500 |
| 37 | 2090 |
| 38 | 5000 |
| 39 | 5000 |
| 40 | 3118 |
| 41 | 673 |
| 42 | 172 |
| 43 | 1909 |
| 44 | 766 |
| 45 | 5000 |
| 46 | 4900 |
| 47 | 5000 |
| 48 | 3924 |
| 49 | 3137 |
| 50 | 2106 |
| 51 | 3111 |
| 52 | 2600 |
| 53 | 5000 |
| 54 | 5000 |
| 55 | 2500 |
| 56 | 5000 |
| 57 | 5000 |
| 58 | 5000 |
| 59 | 5000 |
| 60 | 5000 |
| 61 | 1117 |
| 62 | 5000 |
| 63 | 5000 |
| 64 | 5000 |
| 65 | 5000 |
| 66 | 5000 |
| 67 | 5000 |
| 68 | 5000 |
| 69 | 5000 |
| 70 | 2392 |
| 71 | 5000 |
| 72 | 2546 |
| 73 | 4099 |
| 74 | 2551 |
| 75 | 2837 |
| 76 | 1415 |
| 77 | 492 |
| 78 | 1652 |
| 79 | 2107 |
| 80 | 1646 |
| 81 | 5000 |
| 82 | 2672 |
| 83 | 1738 |
| 84 | 1455 |
| 85 | 5000 |
| 86 | 4499 |
| 87 | 5000 |
| 88 | 5000 |
| 89 | 1769 |
| 90 | 777 |
| 91 | 5000 |
| 92 | 1199 |
| 93 | 4600 |
| 94 | 1997 |
| 95 | 367 |

Method of Use

The compounds of the invention are effective inhibitors of leukotriene A$_4$ hydrolase (LTA4H) and thus inhibit leukotriene production. Therefore, in one embodiment of the invention, there is provided a method of treating leukotriene-mediated disorders using compounds of the invention. In another embodiment, there is provided a method of treating cardiovascular, inflammatory, allergic, pulmonary and fibrotic diseases, renal diseases and cancer using compounds of the invention.

In one embodiment, the invention relates to the use of a compound of the invention for the preparation of a medicament for the treatment leukotriene-mediated disorders. In another embodiment, the invention relates to the use of a compound of the invention, for the preparation of a medicament for treating cardiovascular, inflammatory, allergic, pulmonary and fibrotic diseases, renal diseases and cancer.

In one embodiment, the invention relates to a compound of the invention for use as a medicament for the treatment leukotriene-mediated disorders. In another embodiment, the invention relates to a compound of the invention for use in a method of treating cardiovascular, inflammatory, allergic, pulmonary and fibrotic diseases, renal diseases and cancer.

Without wishing to be bound by theory, by inhibiting the activity of LTA4H, the compounds of the invention block the production of LTB$_4$ resulting from the oxidation of arachidonic acid by 5-LO and subsequent metabolism. Thus, the inhibition of LTA4H activity is an attractive means for preventing and treating a variety of diseases mediated by LTB$_4$. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection, inflammatory and allergic ocular diseases;

Cancer including solid tumors, leukemias and lymphomas; and Renal diseases such as glomerulonephritis.

In one embodiment, the invention relates to a method of treating a leukotriene-mediated disorder comprising administering to a be patient in need thereof one or more of the compounds of the invention, or a pharmaceutically acceptable salt thereof.

In another embodiment, the invention relates to a method of treating a cardiovascular disease comprising administering to a be patient in need thereof one or more of the compounds of the invention, or a pharmaceutically acceptable salt thereof.

In another embodiment, the invention relates to a method of treating a cardiovascular disease comprising administering to a be patient in need thereof one or more of the compounds of the invention, or a pharmaceutically acceptable salt thereof, wherein the cardiovascular disease is selected from atherosclerosis, myocardial infarction, stroke, aortic aneurysm, sickle cell crisis, ischemia-reperfusion injury, pulmonary arterial hypertension and sepsis.

In another embodiment, the invention relates to a method of treating atherosclerosis comprising administering to a be patient in need thereof one or more of the compounds of the invention, or a pharmaceutically acceptable salt thereof.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

In one embodiment, the invention relates to a pharmaceutical composition comprising a pharmaceutically effective amount of a compound of one or more compounds of the invention, or a pharmaceutically acceptable salt thereof, and an excipient.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:
1. A compound of formula (I):

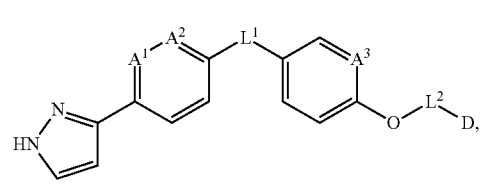

or a pharmaceutically acceptable salt thereof,
wherein:
$A^1$, $A^2$ and $A^3$ are each independently CH or N;
$L^1$ is a linker selected from —O— and —CH$_2$—;
$L^2$ is absent or a —(C$_1$-C$_6$)alkylene-linker; wherein said —(C$_1$-C$_6$)alkylene-linker is optionally substituted with one to three groups selected from —OH, halo, —(C$_1$-C$_6$)alkyl;
D is a ring selected from
(a) —(C$_3$-C$_7$)cycloalkyl, (C$_6$-C$_{10}$)aryl, and -(5- to 11-membered)heteroaryl;
(b) -(4- to 11-membered)heterocycloalkyl, comprising an O or S ring atom and optionally 1 to 3 additional ring heteroatoms selected from N, O, and S;
(c) 4-8 member monocyclic heterocyclic comprising a N ring atom and 1 to 3 additional ring heteroatoms selected from N, O, and S;
(d) a 6 to 11-membered fused bicyclic, bridged bicyclic or spirocyclic heterocyclic radical comprising a N ring atom and optionally 1 to 3 additional ring heteroatoms selected from N, O, and S; and (e) a group selected from 2-oxo-pyrrolidin-1-yl, 2-oxo-pyrrolidin-3-yl, 2-oxo-pyrrolidin-5-yl, 1-methyl-2-oxo-pyrrolidin-4-yl, and 2-oxo-piperidin-5-yl
wherein each of said D rings is optionally substituted with one to three $R^1$ groups; and wherein each of said D rings is further optionally substituted, where possible, by one or two groups independently selected from (=O) and (=S);
each $R^1$ is independently selected from halo, —OH, —$CF_3$, —CN, —($C_1$-$C_6$)alkyl, —O($C_1$-$C_6$)alkyl, —C(O)$R^2$, —C(O)O$R^2$, —C(O)N($R^2$)$_2$, —N($R^2$)$_2$, —N($R^2$)C(O)$R^2$, —S(O)$_2R^2$, —N($R^2$)—S(O)$_2$—$R^2$, —($C_3$-$C_6$)cycloalkyl, -(5- to 11-membered)heterocycloalkyl, —($C_6$-$C_{10}$)aryl, and -(5- to 11-membered)heteroaryl; wherein each of said, —($C_1$-$C_6$)alkyl, —O($C_1$-$C_6$)alkyl, —($C_3$-$C_6$)cycloalkyl, -(5- to 11-membered)heterocycloalkyl, —($C_6$-$C_{10}$)aryl, and -(5- to 11-membered)heteroaryl of said $R^1$ group is optionally substituted with one to three groups selected from halo, —OH, —$CF_3$, —($C_1$-$C_6$)alkyl, —C(O)OH, —C(O)O$C_1$-$C_6$)alkyl, —C(O)($C_1$-$C_6$)alkyl), —$NH_2$, —NH($C_1$-$C_6$)alkyl, N(($C_1$-$C_6$)alkyl)$_2$ and —CN;
each $R^2$ is independently selected from the group consisting of —H, —($C_1$-$C_6$)alkyl, —($C_3$-$C_6$)cycloalkyl, -(5- to 11-membered)heterocycloalkyl, —($C_6$-$C_{10}$)aryl, and -(5- to 11-membered)heteroaryl; wherein each of said, —($C_1$-$C_6$)alkyl, —O($C_1$-$C_6$)alkyl, —($C_3$-$C_6$)cycloalkyl, -(5- to 11-membered)heterocycloalkyl, —($C_6$-$C_{10}$)aryl, and -(5- to 11-membered)heteroaryl of said $R^2$ group is optionally independently substituted by one to three groups selected from halo, —OH, —$CF_3$, —($C_1$-$C_6$)alkyl, —$NH_2$, —NH($C_1$-$C_6$)alkyl, —N(($C_1$-$C_6$)alkyl)$_2$ and —CN.

2. The compound of claim 1, or a pharmaceutically acceptable salt thereof, wherein $A^1$, $A^2$ and $A^3$ are each CH.

3. The compound of claim 1, or a pharmaceutically acceptable salt thereof, wherein $A^1$ and $A^3$ are each CH, and $A^2$ is N.

4. The compound of claim 1, or a pharmaceutically acceptable salt thereof, wherein $A^1$ and $A^2$ are each CH, and $A^3$ is N.

5. The compound of claim 1, or a pharmaceutically acceptable salt thereof, wherein $A^2$ and $A^3$ are each CH, and $A^1$ is N.

6. The compound of claim 1, or a pharmaceutically acceptable salt thereof, wherein $L^1$ is —O—.

7. The compound of claim 1, or a pharmaceutically acceptable salt thereof, wherein $L^1$ is —$CH_2$—.

8. The compound of claim 1, or a pharmaceutically acceptable salt thereof, wherein $L^2$ is absent.

9. The compound of claim 1, or a pharmaceutically acceptable salt thereof, wherein $L^2$ is a —($C_1$-$C_6$)alkylene-linker; and wherein said —($C_1$-$C_6$)alkylene-linker is optionally substituted with one to three groups selected from —OH, halo, —($C_1$-$C_6$)alkyl.

10. The compound of claim 1, or a pharmaceutically acceptable salt thereof, wherein $L^2$ is methylene, ethylene, or propylene; and wherein each of said methylene, ethylene and propylene is optionally substituted with methyl.

11. The compound of claim 1, or a pharmaceutically acceptable salt thereof, wherein said D is a ring selected from —($C_3$-$C_7$)cycloalkyl, ($C_6$-$C_{10}$)aryl, and -(5- to 11-membered)heteroaryl; wherein each of said —($C_3$-$C_7$)cycloalkyl, ($C_6$-$C_{10}$)aryl, and -(5- to 11-membered)heteroaryl is optionally substituted with one to three $R^1$ groups; and wherein each of said —($C_3$-$C_7$)cycloalkyl, ($C_6$-$C_{10}$)aryl, and -(5- to 11-membered)heteroaryl is further optionally substituted, where possible, by one or two groups independently selected from (=O) and (=S).

12. The compound of claim 1, or a pharmaceutically acceptable salt thereof, wherein said ring D is a -(4- to 11-membered)heterocycloalkyl comprising an O or S ring atom and optionally 1 to 3 additional ring heteroatoms selected from N, O, and S; wherein said -(4- to 11-membered)heterocycloalkyl is optionally substituted with one to three $R^1$ groups; and wherein said -(4- to 11-membered)heterocycloalkyl is further optionally substituted, where possible, by one or two groups independently selected from (=O) and (=S).

13. The compound of claim 1, or a pharmaceutically acceptable salt thereof, wherein said ring D is a 4-8 member monocyclic heterocyclic comprising a N ring atom and 1 to 3 additional ring heteroatoms selected from N, O, and S; wherein said 4-8 member monocyclic heterocyclic is optionally substituted with one to three $R^1$ groups; and wherein said 4-8 member monocyclic heterocyclic is further optionally substituted, where possible, by one or two groups independently selected from (=O) and (=S).

14. The compound of claim 1, or a pharmaceutically acceptable salt thereof, wherein said ring D is a 6 to 11-membered fused bicyclic, bridged bicyclic or spirocyclic heterocyclic radical comprising a N ring atom and optionally 1 to 3 additional ring heteroatoms selected from N, O, and S; wherein said 6 to 11-membered fused bicyclic, bridged bicyclic or spirocyclic heterocyclic radical is optionally substituted with one to three $R^1$ groups; and wherein said 6 to 11-membered fused bicyclic, bridged bicyclic or spirocyclic heterocyclic radical is further optionally substituted, where possible, by one or two groups independently selected from (=O) and (=S).

15. The compound of claim 1, wherein said ring D is selected from 2-oxo-pyrrolidin-1-yl, 2-oxo-pyrrolidin-3-yl, 2-oxo-pyrrolidin-5-yl, 1-methyl-2-oxo-pyrrolidin-4-yl, and 2-oxo-piperidin-5-yl; wherein each of said 2-oxo-pyrrolidin-1-yl, 2-oxo-pyrrolidin-3-yl, 2-oxo-pyrrolidin-5-yl, 1-methyl-2-oxo-pyrrolidin-4-yl, and 2-oxo-piperidin-5-yl is optionally substituted with one to three $R^1$ groups; and wherein each of said selected from 2-oxo-pyrrolidin-1-yl, 2-oxo-pyrrolidin-3-yl, 2-oxo-pyrrolidin-5-yl, 1-methyl-2-oxo-pyrrolidin-4-yl, and 2-oxo-piperidin-5-yl is further optionally substituted, where possible, by one or two groups independently selected from (=O) and (=S).

16. The compound of claim 1, or a pharmaceutically acceptable salt thereof, wherein said ring D is selected from:

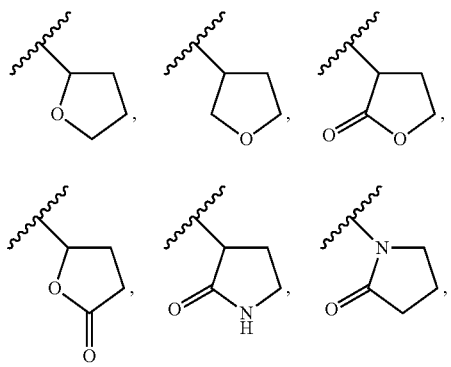

wherein each of the aforementioned D rings is optionally substituted by one to three $R^1$ groups.

17. The compound of claim 1, or a pharmaceutically acceptable salt thereof, wherein $L^2$ and D taken together represent a group selected from:
(1-methyl-pyrrolidin-2-on-4-yl)methyl;
(pyrrolidin-2-on-3yl)oxy;
(pyrrolidin-2-on-5-yl)methyloxy;
2-(pyrrolidin-2-on-1-yl)ethyloxy;
3-(pyrrolidin-2-on-1-yl)propyloxy;
(tetrahydrofuran-3-yl)oxy;
(tetrahydrofuran-2-yl)methyloxy;
(tetrahydrofuran-3-yl)methyloxy; (piperidin-2-on-5-yl)oxy;
(1,3-oxazolidin-2-on-4-yl)methyloxy;
(1,3-oxazolidin-2-on-5-yl)methyloxy;
(morpholin-3-yl)methyloxy;
(morpholin-4-yl)ethyloxy;
1H-pyrazol-5-yl;
(1H-pyrazol-5-yl)methyloxy;
(1H-pyrazol-3-yl)methyloxy;
(1-methyl-1H-pyrazol-3-yl)methyloxy;
(1-methyl-1H-pyrazol-5-yl)methyloxy;
(1-methyl-2-(2-furyl)-pyrazol-5-yl)methyloxy;
3-(1H-pyrazol-1-yl)-ethyloxy;
2-(1H-pyrazol-4-yl)-ethyloxy;
3-(1H-pyrazol-1-yl)-3-methylpropyloxy;
(furan-2-yl)methyloxy;
(furan-3-yl)methyloxy;
(dihydrofuran-2(3H)-on-3-yl)oxy;
(dihydrofuran-2(3H)-on-5-yl)methyloxy;

(pyridin-3-yl)methyloxy;
(pyridin-4-yl)methyloxy;
(2-(1H-pyrazol-1-yl)-pyridin-5-yl)methyloxy;
1-(pyridin2-yl)-ethyloxy;
2-(pyridin-2-yl)ethyloxy;
2-(pyridin-3-yl)ethyloxy;
2-(pyridin-4-yl)-ethyloxy;
(pyrimidin-2-yl)methyloxy;
(thien-3-yl)methyloxy;
2-(thien-2-yl)ethyloxy;
(tetrahydro-2H-pyran-3-yl)oxy;
(tetrahydro-2H-pyran-4-yl)oxy);
(tetrahydro-2H-pyran-2-yl)methyloxy;
(tetrahydro-2H-pyran-3-yl)methyloxy;
(tetrahydro-2H-pyran-4-yl)methyloxy;
2-(tetrahydro-2H-pyran-2-yl)ethyloxy;
2-(tetrahydro-2H-pyran-4-yl)ethyloxy;
(2-methyl-1H-imidazol-1-yl)ethyloxy;
(pyrazin-2-yl)methyloxy;
benzyloxy;
(4-(methylsulfonyl)benzyl)oxy;
(1,3-thiazol-2-yl)methyloxy;
(1,3-thiazol-5-yl)methyloxy;
2-(1,3-thiazol-5-yl)ethyloxy;
(4-methyl-1,2,3-thiadiazol-5-yl)methyloxy;
(isoxazol-5-yl)methyloxy;
2-(isoxazol-4-yl)ethyloxy;
(1-methyl-1,2,4-triazol-5-yl)methyloxy;
(1,3-oxazol-4-yl)methyloxy;
(1,3-oxazol-5-yl)methyloxy;
(2-methyl-1,3-oxazol-4-yl)methyloxy;
(4-methyl-1,3-oxazol-5-yl)methyloxy;
(1H-benzimidazol-2-yl)methyloxy;
(1H-benzimidazol-5-yl)methyloxy;
(1H-benzimidazol-1-yl)ethyloxy;
(1H-benzimidazol-2-yl)ethyloxy;
2-((1H-benzimidazol-2-yl)-amino)ethyloxy;
(imidazo[2,1-b][1,3]thiazol-2-yl)methyloxy;
(1H-pyrrolo[2,3-b]pyridin-5-yl)methyloxy;
(6,7-dihydro-5H-cyclopenta[b]pyridin-7-yl)oxy;
2-(1H-pyrrolo[3,2-b]pyridin-6-yl)-ethyloxy;
(imidazo[1,2-a]pyridin-2-yl)methyloxy;
(1,3-benzothiazol-2-yl)methyloxy; and
(imidazo[1,2-a]pyridin-6-yl)methyloxy.

18. A pharmaceutical composition comprising the compound of claim 1, or a pharmaceutically acceptable salt thereof, and a pharmaceutically acceptable carrier or excipient.

19. A method of treating a cardiovascular disease comprising administering to a compound of claim 1, or a pharmaceutically acceptable salt thereof, to a patient in need thereof.

* * * * *